US009346728B2

(12) United States Patent
Keusenkothen et al.

(10) Patent No.: US 9,346,728 B2
(45) Date of Patent: May 24, 2016

(54) HYDROCARBON CONVERSION PROCESS

(75) Inventors: Paul F. Keusenkothen, Houston, TX (US); Frank Hershkowitz, Basking Ridge, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 13/993,194

(22) PCT Filed: Dec. 20, 2011

(86) PCT No.: PCT/US2011/066174
§ 371 (c)(1),
(2), (4) Date: Sep. 18, 2013

(87) PCT Pub. No.: WO2012/099673
PCT Pub. Date: Jul. 26, 2012

(65) Prior Publication Data
US 2014/0296570 A1 Oct. 2, 2014

Related U.S. Application Data

(60) Provisional application No. 61/434,410, filed on Jan. 19, 2011, provisional application No. 61/434,417, filed on Jan. 19, 2011, provisional application No. 61/434,411, filed on Jan. 19, 2011, provisional application No. 61/434,419, filed on Jan. 19, 2011, provisional application No. 61/434,415, filed on Jan. 19, 2011, provisional application No. 61/434,413, filed on Jan. 19, 2011, provisional application No. 61/434,409, filed on Jan. 19, 2011, provisional application No. 61/481,999, filed on May 3, 2011, provisional application No. 61/500,854, filed on Jun. 24, 2011, provisional application No. 61/504,611, filed on Jul. 5, 2011.

(30) Foreign Application Priority Data

Aug. 9, 2011 (EP) .................................... 11177021

(51) Int. Cl.
| C07C 29/16 | (2006.01) |
| C07C 45/50 | (2006.01) |
| C07C 1/20 | (2006.01) |
| C07C 1/24 | (2006.01) |
| C07C 2/76 | (2006.01) |
| C07C 5/09 | (2006.01) |
| C07C 2/40 | (2006.01) |
| C07C 2/48 | (2006.01) |
| C07C 2/84 | (2006.01) |
| C07C 11/04 | (2006.01) |
| C07C 11/12 | (2006.01) |
| C07C 11/21 | (2006.01) |
| C07C 15/04 | (2006.01) |
| C07C 15/06 | (2006.01) |
| C07C 29/48 | (2006.01) |
| C07C 31/10 | (2006.01) |
| C07C 47/02 | (2006.01) |
| C07C 51/14 | (2006.01) |

(52) U.S. Cl.
CPC .................. *C07C 45/505* (2013.01); *C07C 1/20* (2013.01); *C07C 1/24* (2013.01); *C07C 2/403* (2013.01); *C07C 2/48* (2013.01); *C07C 2/76* (2013.01); *C07C 2/84* (2013.01); *C07C 5/09* (2013.01); *C07C 11/04* (2013.01); *C07C 11/12* (2013.01); *C07C 11/21* (2013.01); *C07C 15/04* (2013.01); *C07C 15/06* (2013.01); *C07C 29/16* (2013.01); *C07C 29/48* (2013.01); *C07C 31/10* (2013.01); *C07C 47/02* (2013.01); *C07C 51/14* (2013.01); *Y02P 30/42* (2015.11)

(58) Field of Classification Search
CPC .......... C07C 29/16; C07C 47/21; C07C 51/14
See application file for complete search history.

(56) References Cited

U.S. PATENT DOCUMENTS

| 1,134,677 A | 4/1915 | Heinemann |
| 1,860,624 A | 5/1932 | Sauerwein |
| 2,319,679 A | 5/1943 | Hasche et al. |
| 2,678,339 A | 5/1954 | Harris |
| 2,692,819 A | 10/1954 | Hasche et al. |
| 3,024,094 A | 3/1962 | Coberly |
| 3,093,697 A | 6/1963 | Kasbohm et al. |
| 3,156,733 A | 11/1964 | Happel et al. |
| 3,242,223 A | 3/1966 | Nonnenmacher et al. |
| 3,419,632 A | 12/1968 | Sogawa et al. |
| 3,617,495 A | 11/1971 | Zimmerman, Jr. et al. |

(Continued)

FOREIGN PATENT DOCUMENTS

| BE | 722895 | 10/1968 |
| DE | 875198 | 4/1953 |

(Continued)

OTHER PUBLICATIONS

Watt, L., "The Production of Acetylene from Methane by Partial Oxidation", Thesis University OG British Columbia, Sep. 1, 1951, pp. 1-50.

(Continued)

*Primary Examiner* — Yong Chu
*Assistant Examiner* — Ana Z Muresan

(57) ABSTRACT

The invention relates to a process for converting hydrocarbons into products containing aldehydes and/or alcohols. The invention also relates to producing olefins from the aldehyde and alcohol, to polymerizing the olefins, and to equipment useful for these processes.

15 Claims, 5 Drawing Sheets

(56) References Cited

U.S. PATENT DOCUMENTS

| | | |
|---|---|---|
| 3,644,555 A | 2/1972 | Nagy et al. |
| 3,839,484 A | 10/1974 | Zimmerman, Jr. et al. |
| 4,274,841 A | 6/1981 | Andresen et al. |
| 5,675,041 A | 10/1997 | Kiss et al. |
| 5,856,592 A | 1/1999 | Hagen |
| RE36,563 E * | 2/2000 | Takeuchi ............... 526/134 |
| 6,049,011 A | 4/2000 | Kiss et al. |
| 6,121,503 A | 9/2000 | Janssen et al. |
| 6,177,600 B1 | 1/2001 | Netzer |
| 6,210,561 B1 | 4/2001 | Bradow et al. |
| 6,307,093 B1 | 10/2001 | Godwin et al. |
| 6,578,378 B2 | 6/2003 | Kaiser et al. |
| 7,045,670 B2 | 5/2006 | Johnson et al. |
| 7,115,789 B2 | 10/2006 | Kuechler et al. |
| 7,119,240 B2 | 10/2006 | Hall et al. |
| 7,138,047 B2 | 11/2006 | Stell et al. |
| 7,208,647 B2 | 4/2007 | Peterson et al. |
| 7,491,250 B2 | 2/2009 | Hershkowitz et al. |
| 7,815,873 B2 | 10/2010 | Sankaranarayanan et al. |
| 7,846,401 B2 | 12/2010 | Hershkowitz et al. |
| 7,943,808 B2 | 5/2011 | Hershkowitz et al. |
| 8,158,837 B2 | 4/2012 | Mamadov et al. |
| 8,440,070 B2 | 5/2013 | Keusenkothen |
| 2002/0000085 A1 | 1/2002 | Hall et al. |
| 2002/0098430 A1 | 7/2002 | Kawamura et al. |
| 2004/0002553 A1 | 1/2004 | Hall et al. |
| 2004/0192982 A1 | 9/2004 | Kuechler et al. |
| 2007/0090018 A1 | 4/2007 | Keusenkothen et al. |
| 2007/0090019 A1 | 4/2007 | Keusenkothen et al. |
| 2007/0090020 A1 | 4/2007 | Buchanan et al. |
| 2007/0191664 A1 | 8/2007 | Hershkowitz et al. |
| 2008/0142049 A1 | 6/2008 | Onishi et al. |
| 2008/0300438 A1 | 12/2008 | Keusenkothen et al. |
| 2010/0130803 A1 | 5/2010 | Keusenkothen et al. |
| 2010/0292523 A1 | 11/2010 | Hershkowitz et al. |

FOREIGN PATENT DOCUMENTS

| | | |
|---|---|---|
| DE | 1270537 | 6/1968 |
| DE | 2354217 | 5/1975 |
| EP | 1288182 | 3/2003 |
| EP | 1741691 | 1/2007 |
| EP | 2022772 | 2/2009 |
| GB | 795688 | 5/1958 |
| GB | 834419 | 5/1960 |
| GB | 846679 | 8/1960 |
| GB | 1007423 | 10/1965 |
| GB | 1090983 | 11/1967 |
| WO | 2005/097948 | 10/2005 |
| WO | 2011/008389 | 1/2011 |
| WO | 2012/099679 | 7/2012 |

OTHER PUBLICATIONS

SRI Consulting Process Economics Program "Acetylene" Report 16 (1966) and 16A (1982).

Energy Fuels, 2007, 21(2), pp. 640-645.

* cited by examiner

HYDROCARBON CONVERSION PROCESS

CROSS-REFERENCE TO RELATED APPLICATIONS

This application claims priority from U.S. Provisional Application Ser. No. 61/500,854, filed Jun. 24, 2011 and European Patent Application No. 11177021.0 filed Aug. 9, 2011, each being incorporated by reference herein in its entirety. This application is the National Stage of International Patent Application No. PCT/US2011/066174, filed Dec. 20, 2011, which is incorporated by reference herein in its entirety. This application also claims priority from U.S. Provisional Application Ser. No. 61/434,409, filed Jan. 19, 2011, U.S. Provisional Application Ser. No. 61/434,410, filed Jan. 19, 2011, U.S. Provisional Application Ser. No. 61/434,411, filed Jan. 19, 2011, U.S. Provisional Application Ser. No. 61/434,413, filed Jan. 19, 2011, U.S. Provisional Application Ser. No. 61/434,415, filed Jan. 19, 2011, U.S. Provisional Application Ser. No. 61/434,417, filed Jan. 19, 2011, U.S. Provisional Application Ser. No. 61/434,419, filed Jan. 19, 2011, U.S. Provisional Application Ser. No. 61/481,999, filed May 3, 2011, and Provisional Application Ser. No. 61/504,611, filed Jul. 5, 2011, the contents of each of which are incorporated by reference in their entirety. Reference is made to the following related cases, each being incorporated by reference in its entirety: PCT/US2011/066216, filed Dec. 20, 2011, PCT/US2011/066202, filed Dec. 20, 2011; PCT/US2011/066210, filed Dec. 20, 2011; PCT/US2011/066196, filed Dec. 20, 2011; PCT/US2011/066152, filed Dec. 20, 2011; PCT/US2011/066186, filed Dec. 20, 2011; PCT/US2011/066206, filed Dec. 20, 2011; PCT/US2011/066180, filed Dec. 20, 2011; and PCT/US2011/066165, filed Dec. 20, 2011.

FIELD

The invention relates to processes for converting hydrocarbons into products containing aldehydes and/or alcohols. The invention also relates to producing olefins from the aldehydes and alcohols, to polymerizing the olefins, and to equipment useful for these processes.

BACKGROUND

Olefins, such as propylene, are commonly used for producing polymers, such as polypropylene. Propylene can be produced. e.g., by steam cracking; propanol dehydrogenation, the propanol being derived from propionaldehyde (also known as propanal) for example; etc.

Propanol and propanal can be produced using hydroformylation, e.g., by contacting syngas and $C_2$ unsaturates such as ethylene with a hydroformylation catalyst according to the following equation:

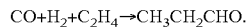

$$CO+H_2+C_2H_4 \rightarrow CH_3CH_2CHO.$$

The propanal can be hydrogenated to produce the propanol. Although the $C_2$ unsaturates can be manufactured in conventional processes such as steam cracking, hydrocracking, and fluid catalytic cracking, the amount of hydrogen and carbon monoxide available in the product of those processes is not sufficient for hydroformylating a significant amount of the $C_2$ unsaturates. Consequently, commercial hydroformylation processes, such as the "Oxo" process, utilize an external syngas source, such as a steam reforming or hydrocarbon partial oxidation process.

There is therefore a need for a process for producing $C_2$ unsaturates and sufficient hydrogen and carbon monoxide to hydroformylate the $C_2$ unsaturates to propanal and propanol.

SUMMARY

The invention relates to a hydrocarbon conversion process, comprising:
(a) providing a first mixture, the first mixture comprising hydrocarbon and oxygenate;
(b) exposing the first mixture a temperature ≥700° C. in a first region under thermal pyrolysis conditions to produce a second mixture, the second mixture comprising molecular hydrogen, carbon monoxide, and ≥1.0 wt. % of $C_2$ unsaturates based on the weight of the second mixture, wherein the second mixture has a CO:$C_2$ unsaturates molar ratio in the range of 0.1 to 2.0;
(c) transferring to at least one converter (i) at least a portion of the second mixture and/or (ii) a third mixture derived from the second mixture, the transferred mixture comprising hydrogen, carbon monoxide, and ≥1.0 wt. % of $C_2$ unsaturates based on the weight of the transferred mixture, wherein the transferred mixture has a CO:$C_2$ unsaturates molar ratio in the range of 0.1 to 2.0; and
(d) converting ≥10.0 wt. % of the transferred mixture's $C_2$ unsaturates, based on the weight of the transferred mixture's $C_2$ unsaturates, to form a product comprising ≥1.0 wt. % of $C_{3+}$ aldehyde and/or ≥1.0 wt. % $C_{3+}$ alcohol based on the weight of the product.

In another embodiment, a hydrocarbon conversion process, comprising
(a) providing a first mixture comprising hydrocarbon and oxygenate;
(b) exposing the first mixture to a temperature ≥1.4×10³° C. at a total pressure ≥0.1 bar (absolute) under high-severity thermal pyrolysis conditions in a first region to produce a second mixture, the second mixture comprising molecular hydrogen, carbon monoxide, ≥1.0 wt. % ethylene, and ≥1.0 wt. % of acetylene based on the weight of the second mixture, the second mixture having an acetylene:ethylene molar ratio in the range of 0.5 to 20.0 and a carbon monoxide:$C_2$ unsaturates molar ratio in the range of 0.15 to 2.0:
(c) transferring the second mixture away from the first region;
(d) providing a fourth mixture comprising fuel and oxidant, and at least partially oxidizing the fourth mixture in a second region to produce a fifth mixture comprising water and/or carbon dioxide, the first and second regions being at least partially coextensive and the oxidizing being conducted at a substantially different time than the exposing;
(e) transferring the fifth mixture away from the second region;
(f) separating from the second mixture (i) a third mixture having a CO:$C_2$ unsaturates ratio in the range of 0.15 to 2.0 and comprising molecular hydrogen, carbon monoxide, methane, and ≥1.0 wt. % ethylene based on the weight of the third mixture and (ii) a composition comprising >90.0% of the second mixture's acetylene:
(g) hydroformylating at least a portion of the third mixture to produce a product comprising ≥1.0 wt. % $C_{3+}$ aldehyde and/or 1.0 wt. % $C_{3+}$ alcohol based on the weight of the product; and
(h) converting at least a portion of the composition to one or more of ethylene, ethylene glycol, acetic acid, acrylic acid, benzene, toluene, or xylene, styrene, or butadiene; wherein:
(i) steps (a)-(e) are conducted in sequence continuously or semi-continuously; and/or (ii) heat is provided to the coextensive portion of the first region, at least a portion of the heat being derived from the oxidizing of step (d).

In yet another embodiment, a hydrocarbon conversion process, comprising:
(a) providing a first mixture comprising hydrocarbon and oxygenate;
(b) exposing the first mixture to a temperature $\geq 1.40 \times 10^{3\circ}$ C. at a total pressure $\geq 0.1$ bar (absolute) under high-severity thermal pyrolysis conditions in a first region to produce a second mixture, the second mixture comprising molecular hydrogen, carbon monoxide, $\geq 1.0$ wt. % ethylene, and $\geq 1.0$ wt. % of acetylene based on the weight of the second mixture, the second mixture having an acetylene:ethylene molar ratio in the range of 0.5 to 20.0 and a carbon monoxide:$C_2$ unsaturates molar ratio in the range of 0.10 to 2.0;
(c) transferring the second mixture away from the first region, dividing the second mixture into first and second portions, and deriving a third mixture from the first portion; the third mixture (i) comprising carbon monoxide and $\geq 1.0$ wt. % of acetylene based on the weight of the third mixture and (ii) having a CO:$C_2$ unsaturates molar ratio in the range of 0.15 to 2.0 and a molecular hydrogen:acetylene molar ratio$\geq 0.75$;
(d) providing a fourth mixture comprising fuel and oxidant, and at least partially oxidizing the fourth mixture in a second region to heat the first region and to produce a fifth mixture comprising water and/or carbon dioxide, the first and second regions being at least partially coextensive and the oxidizing being conducted at a substantially different time than the exposing,
(e) transferring the fifth mixture away from the second region;
(f) hydroformylating at least a portion of the third mixture to form a first product comprising $\geq 1.0$ wt. % of $C_{3+}$ aldehyde and/or $\geq 1.0$ wt. % $C_{3+}$ alcohol based on the weight of the product; and
(g) converting at least a portion of the second portion to form a second product comprising $\geq 2.0$ wt. % ethylene and $\leq 1.0$ wt. % $C_{3+}$ unsaturates based on the weight of the second product.

In yet another embodiment, the invention relates to a hydrocarbon conversion process, comprising:
converting a first mixture to a second mixture, the first mixture having a first STP enthalpy $H_i$ and comprising hydrocarbon and oxygenate and the second mixture having a carbon monoxide:$C_2$ unsaturates molar ratio$\geq 0.50$ and a second STP enthalpy $H_o$; wherein (a) the second mixture comprises carbon monoxide, ethylene, and $\geq 1.0$ wt. % of acetylene based on the weight of the second mixture; (b), the second mixture has a molecular hydrogen:acetylene molar ratio$\geq 0.75$; and (c) $H_o-H_i \geq 0.0$ kcal per mole of hydrocarbon in the first mixture; and then
catalytically converting at least a portion of the second mixture to form a product comprising $\geq 1.0$ wt. % of $C_{3+}$ aldehyde and/or $C_{3+}$ alcohol based on the weight of the product.

DETAILED DESCRIPTION

Figure 1:
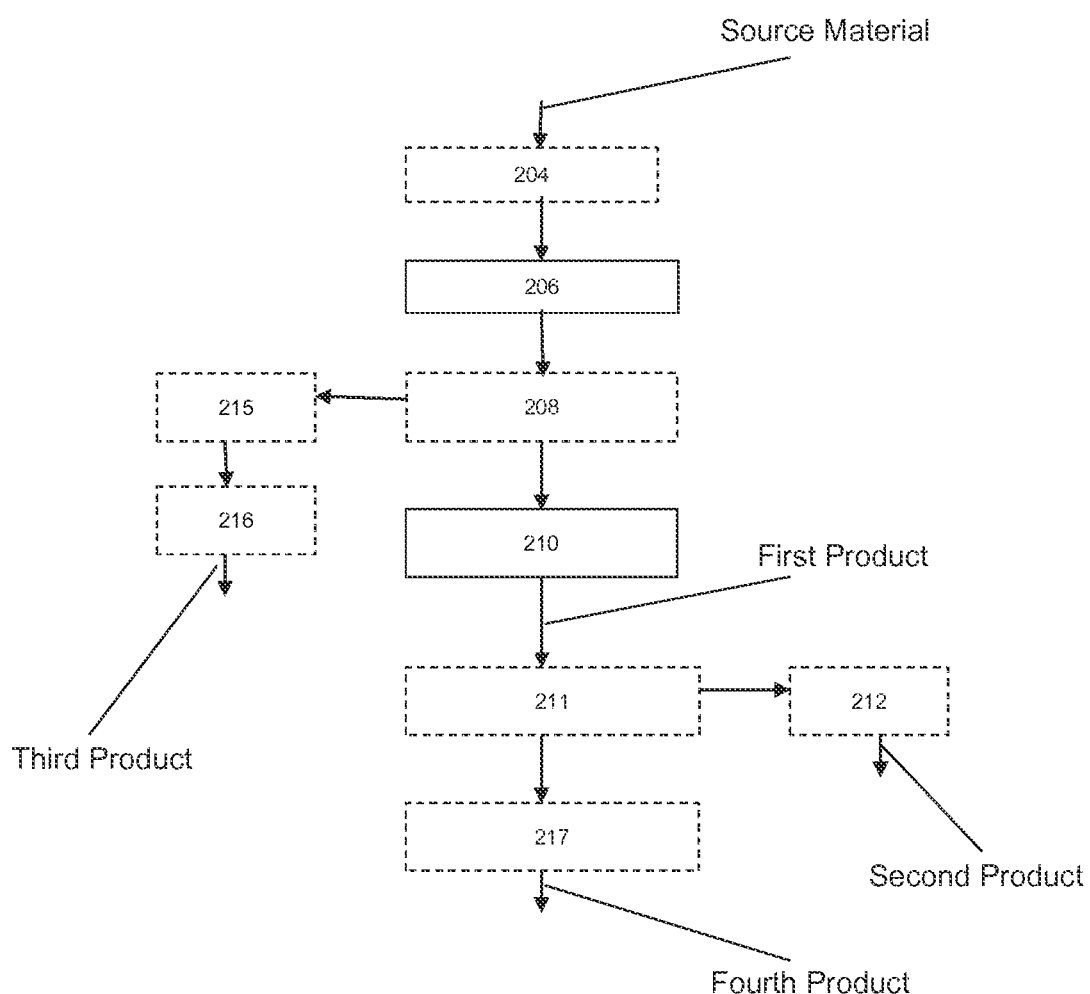
FIG. 1 schematically illustrates embodiments of the invention relating to the conversion of hydrocarbon and oxygenate to a product comprising propanal and/or propanol, optional stages are enclosed by dashed lines.

The invention is based in part on the discovery of a process for converting a first mixture comprising hydrocarbon and oxygenate to a second mixture comprising $C_2$ unsaturates and syngas in relative amounts that are useful for producing $C_{3+}$ aldehydes and $C_{3+}$ alcohols, e.g., by hydroformylation. The process involves exposing the first mixture under thermal pyrolysis conditions to a temperature $\geq 700°$ C. (which as used herein means $0.70 \times 10^{3\circ}$ C., i.e., two significant digits), e.g., $\geq 1.20 \times 10^{3\circ}$ C. This results in (i) the conversion of a significant amount of the hydrocarbon in the first mixture to $C_2$ unsaturates and (ii) the conversion of a significant amount of hydrocarbon and oxygenate in the first mixture to carbon monoxide, instead of higher molecular weight (and less useful) oxygen-containing compositions such as carbon dioxide. The process further comprises converting at least a portion of $C_2$ unsaturates present in a third mixture to a product comprising $C_{3+}$ aldehydes and/or $C_{3+}$ alcohols, the third mixture being derived from the second mixture, e.g., in one or more upgrading stages. For example, in an embodiment, the second mixture comprises $\geq 1.0$ wt. % of $C_2$ unsaturates, $\geq 0.5$ wt. % carbon monoxide, and $\geq 0.1$ wt. % hydrogen based on the weight of the second mixture, wherein the second mixture has a CO:$C_2$ unsaturates molar ratio in the range of 0.10 to 2.0. The second and third mixtures can each comprise a substantially stoichiometric amount of carbon monoxide and hydrogen, e.g., amounts approximately equal the amounts needed for hydroformylating at least a portion of the $C_2$ unsaturates therein, to produce a product comprising $C_{3+}$ aldehydes and/or $C_{3+}$ alcohols. For example, the third mixture can have a carbon monoxide to $C_2$ unsaturates molar ratio$\geq 0.10$, e.g., in the range of 0.15 to 1.2. Optionally, at least a portion of the $C_{3+}$ aldehydes and $C_{3+}$ alcohols derived from the third mixture are converted to $C_{3+}$ olefin, e.g., by cracking, dehydration or dehydrogenation. Optionally, at least a portion of the $C_{3+}$ aldehydes are converted to $C_{3+}$ alcohol before the olefin conversion. Polymerizing at least a portion of the olefin resulting from the olefin conversion is within the scope of the invention. If desired, at least a portion of the pyrolysis heat utilized in deriving the second mixture from the first mixture can be provided by exothermically reacting (e.g., combusting) a fourth mixture which produces a fifth mixture comprising products of the exothermic reaction. Deriving the third mixture from the second mixture can involve combining desired species with the second mixture and/or separating undesired species.

For the purpose of this description and appended claims, the following terms are defined. The term "hydrocarbon" means molecules (and mixtures thereof) including both carbon atoms and hydrogen atoms, and optionally including other atoms (heteroatoms) such as oxygen, sulfur, and nitrogen, wherein the carbon atoms and hydrogen atoms together comprise ≥75.0% of the atoms present in the molecule or mixture of molecules; but excluding molecules comprising ≥10.0 atom % of oxygen atoms. The term "oxygenate" means (i) oxygen atoms and (ii) molecules (and mixtures thereof) which include at least one oxygen atom wherein the oxygen atoms comprise ≥10.0 atom % based on the number of atoms present in the molecule or mixture of molecules, including those molecules which further comprise hydrogen, carbon, sulfur, and nitrogen. The term "molecular hydrogen" means $H_2$.

The term "$C_{3+}$ aldehyde" means an aldehyde having three or more carbon atoms. The term "$C_{3+}$ alcohol" means an alcohol having three or more carbon atoms. The term "$C_2$ unsaturates" means a hydrocarbon having two carbon atoms and two or four hydrogen atoms. The term "polymer" means a composition including a plurality of macromolecules, the macromolecules containing recurring units derived from one or more monomers. The macromolecules can have different size, molecular architecture, atomic content, etc. The term "polymer" includes macromolecules such as copolymer, terpolymer, etc. "Polyethylene" means polyolefin containing ≥50.0% (by number) recurring ethylene-derived units, preferably polyethylene homopolymer and/or polyethylene copolymer wherein at least 85% (by number) of the recurring units are ethylene-derived units. "Polypropylene" means polyolefin containing >50.0% (by number) recurring propylene-derived units, preferably polypropylene homopolymer and/or polypropylene copolymer wherein at least 85% (by number) of the recurring units are propylene-derived units. The "Periodic Table of the Elements" means the Periodic Chart of the Elements as tabulated on the inside cover of The Merck Index, 12th Edition, Merck & Co., Inc., 1996.

The terms "convert", "conversion", "converting", etc. with respect to pyrolysis processes include, e.g., any molecular decomposition, cracking, breaking apart, reformation of molecules, including hydrocarbon, oxygenate, etc., by at least pyrolysis heat. With respect to non-pyrolysis processes that are at least partly catalytic, the term conversion includes, e.g., hydroprocessing (such as hydrogenation, hydrotreating, etc.), hydroformylation, catalytic separation, etc.

The terms "pyrolysis" and "pyrolysis chemistry" mean an endothermic reaction conducted at a temperature sufficient for thermally breaking C—C or C—H bonds, optionally aided by a catalyst, e.g., the conversion of hydrocarbons to unsaturates such as ethylene and acetylene.

The term "reactor" means equipment and combinations thereof for chemical conversion, including reactor combinations and systems such as disclosed in U.S. Patent App. Pub. No. 2007/0191664. The term "pyrolysis reactor", as used herein, refers to a reactor, or combination or system thereof for converting hydrocarbons by at least pyrolysis. A pyrolysis reactor optionally includes one or more reactors and/or associated equipment and lines. The term pyrolysis reactor encompasses, e.g., the combination and system of first and second pyrolysis reactors described in U.S. Patent App. Pub. No. 2007/0191664. With respect to pyrolysis reactors, the term "residence time" means the average time duration for non-reacting (non-converting by pyrolysis) molecules (such as He, $N_2$, Ar) having a molecular weight in the range of 4 to 40 to traverse a pyrolysis region of a pyrolysis reactor. The term "pyrolysis stage" means at least one pyrolysis reactor, and optionally including means for conducting one or more feeds thereto and/or one or more products away therefrom. With respect to reactors, the term "region" means a location within a reactor, e.g., a specific volume within a reactor, a specific volume between two reactors and/or the combination of different disjointed volumes in one or more reactors. A "pyrolysis region" is a region for conducting pyrolysis. The term "thermal pyrolysis" means <50.0% of the heat utilized by the pyrolysis is provided by (a) exothermically reacting the pyrolysis feed, e.g., by exothermically reacting an oxidant with hydrocarbon and/or hydrogen of the first mixture and/or (b) contacting the pyrolysis feed with the products of combustion to heat the pyrolysis feed. The term "thermal pyrolysis reactor" means a pyrolysis reactor wherein ≥50.0% of the heat utilized by the pyrolysis is provided by heat transfer from reactor components. e.g., solid surfaces associated with the reactor such as tubulars or bed materials; optionally ≥80.0% or ≥90.0% of the heat utilized by the pyrolysis is provided by such heat transfer. Optionally, an exothermic reaction (e.g., combustion) occurs within the thermal pyrolysis reactor, the exothermic reaction providing a major amount (i.e., ≥50.0%) of the endothermic heat of pyrolysis, such as ≥75.0% or ≥90.0% thereof, the exothermic reaction occurring at a different location within the pyrolysis reactor and/or at a different time than the pyrolysis.

The term "high-severity" with respect to the pyrolysis of a feed comprising hydrocarbon, e.g., the first mixture, means pyrolysis operating conditions resulting in the conversion to acetylene of ≥10.0 wt. % of the feed's hydrocarbon based on the total weight of hydrocarbon in the feed. The operating conditions for a thermal pyrolysis reactor may be characterized by a severity threshold temperature that divides low-severity operating conditions in thermal pyrolysis reactors from high-severity operating conditions in thermal pyrolysis reactors. The severity threshold temperature is defined as the lowest temperature at which the feed to the reactor may react at a residence time≤0.1 second to make at least 10.0 wt. % acetylene as a percent of the hydrocarbons in the mixture evaluated at the given operating conditions of the process. The high-severity operating conditions for a thermal pyrolysis reactor may be characterized as peak pyrolysis gas temperatures that are greater than or equal to the severity threshold temperature. The low-severity operating conditions for a thermal pyrolysis reactor may be characterized as peak pyrolysis gas temperatures that are less than the severity threshold temperature and no pyrolysis gas temperatures that exceed the severity threshold temperature. For example, for the thermal conversion of a methane feed at a pressure of 14.7 psig (101 kPa) and with 2:1 molar ratio of molecular hydrogen to methane, the threshold temperature is about 1274° C. for this process. At temperatures at or above 1274° C., yields of acetylene can exceed 10.0 wt. % of feed hydrocarbon, at some time≤0.1 seconds. Conversely, at temperatures below 1274° C., there are no times≤0.1 seconds for which yields of acetylene reach 10.0 wt. % of the methane.

The term "peak pyrolysis gas temperature" means the maximum temperature achieved by the bulk pyrolysis stream gases as they travel through the pyrolysis reactor (e.g., cracking region or radiant region). One skilled in the art will appreciate that temperatures immediately proximate to a solid material may be higher, and may, in some infinitesimal boundary layer, actually approach the solid temperature. However, the pyrolysis temperature referred to herein should be considered a bulk gas temperature, which is a temperature that could be measured by a device (such as a thermocouple) that is not in contact with the solid material. For example, if the gas is a pyrolysis stream traveling through tubulars in a thermal pyrolysis reactor, the bulk gas temperature may be taken as the average temperature over any tubular cross-section, and the peak pyrolysis gas temperature as the highest cross-sectional-average temperature of the pyrolysis stream.

The second mixture is generally produced by pyrolysis of the first mixture, the first mixture being derived from one or more source materials. The term "source materials" means sources comprising hydrocarbon and/or oxygenate. Examples of source materials comprising hydrocarbon include one or more of petroleum-derived streams; syngas (a mixture comprising carbon monoxide and hydrogen), methane; methane-containing streams such as coal bed methane, biogas, associated gas, natural gas, and mixtures or components thereof; synthetic crudes; shale oils; or hydrocarbon streams derived from plant or animal matter. Suitable hydrocarbon source materials include those described in U.S. Pat. Nos. 7,943,808 and 7,544,852, which are incorporated by reference herein in their entirety. Examples of source materials comprising oxygenate include one or more of molecular oxygen, water (e.g., steam), carbon monoxide, carbon dioxide, alcohols (e.g., methanol, ethanol, etc.), acids such as hydrocarbon containing a carboxyl functionality, carbonyls, carbonates, carbamates, carbohydrates, non-volatile oxygenates, etc.

The term "hydrogen content" of a mixture or source material means atomic hydrogen bound to carbon and/or heteroatoms covalently bound thereto and which excludes molecular hydrogen ($H_2$) in the mixture (or source material) expressed as a weight percent based on the weight of the hydrocarbons in the mixture (or source material). Optionally, one or more mixtures and/or source materials comprises non-volatiles. The term "non-volatiles" means molecules and mixtures thereof having a nominal atmospheric boiling point≥570.0° C., e.g., refractory oxygenates, refractory hydrocarbons, metals, minerals, etc. American Society of Testing and Materials ("ASTM") methods can be used to determine the nominal atmospheric boiling point (ASTM method 1078) and the amount and properties of such non-volatiles, such as ASTM methods D-6560, D-7061, D-189. D-482, D-524, and D-2415. Non-volatiles that are capable of being combusted are called "combustible non-volatiles". The term non-volatiles encompasses e.g., coke, ash, soot, resid, metal, mineral, ash-forming asphaltenic, tar, etc., including those formed, e.g., during or after oxidation (e.g., combustion or partial oxidation) and/or pyrolysis, including those which may remain as a residue or deposit in the reaction region. Optionally, one or more mixtures and/or source materials comprises $C_{3+}$. The term "$C_{3+}$" means molecules having at least three carbon atoms, including. e.g., coke and soot, whether those products emerge from the reactor or remain within the pyrolysis reactor.

Suitable reaction conditions; the first, second, third, fourth, and fifth mixtures; and related products and byproducts will now be described in more detail. Although the following embodiments are described in terms of high-temperature thermal pyrolysis reactions, the invention is not limited thereto, and this description is not meant to foreclose other embodiments within the broader scope of the invention.

I. First Mixture

The first mixture generally comprises (i) hydrocarbon and (ii) oxygenate, and optionally further comprises (iii) molecular hydrogen and (iv) diluent, the hydrocarbon and oxygenate being as defined in the preceding section. The type of hydrocarbon is not critical; e.g., the hydrocarbon can even comprise hydrocarbon non-volatiles, including those that are not in the gas phase at the temperature, pressure, and composition conditions subsisting at the inlet to the pyrolysis reactor. Optionally, the first mixture comprises ≥10.0 wt. % hydrocarbon and ≥1.0 wt. % oxygenate based on the weight of the first mixture, e.g., ≥25.0 wt. % hydrocarbon and ≥5.0 wt. % oxygenate, such as ≥50.0 wt. % hydrocarbon and ≥10.0 wt. % oxygenate.

The hydrocarbon and oxygenate of the first mixture can be derived from one or more source materials, as defined in the preceding section. The first mixture can be derived from the source material(s) upstream of the pyrolysis, but this is not required. For example, in one embodiment the first and second source materials are conducted separately to a pyrolysis reactor, wherein (i) the first source material comprises hydrocarbon and (ii) the second source material comprises oxygenate, with the first and second source materials being combined to produce the first mixture proximate to (e.g., within) the pyrolysis reactor. Optionally, a hydrocarbon source material has a hydrogen content in the range of 6.0 wt. % to 25.0 wt. %, 8.0 wt. % to 20.0 wt. % (e.g., not natural gas), or 20.0 wt. % to 25.0 wt. % (e.g., natural gas). In a particular embodiment, the hydrocarbon of the first mixture is derived from natural gas (e.g., a methane-containing gas of synthetic and/or geological origin). The first mixture can comprise, e.g., upgraded natural gas (such as natural gas that has been sweetened and/or dehydrated). Besides methane, natural gas commonly includes other hydrocarbons (such as ethane and other alkanes), generally in amounts greater than or equal to the amount of methane in the natural gas on a weight basis. Optionally, the natural gas further comprises oxygenate (e.g., water, $CO_2$, etc.) and/or diluent (e.g., hydrogen sulfide, nitrogen, etc.), which can be used as a source of at least a portion of the oxygenate (in the case of water and/or $CO_2$) and/or diluent (in the case of nitrogen) in the first mixture. One feature of the invention is that a natural gas containing a significant amount of $CO_2$, e.g., ≥20.0 mole % $CO_2$ per mole of the natural gas, can be converted into technologically important products such as propanal, propanol, and propylene. Optionally, the oxygenate of the first mixture is derived from the same source material as the hydrocarbon (e.g., both the hydrocarbon and oxygenate are derived from natural gas). Alternatively, the oxygenate is derived from at least a second source material. e.g., one comprising one or more of oxygen ($O_2$), water (e.g., steam), carbon monoxide, carbon dioxide, acid (e.g., organic acids such as hydrocarbon containing a carboxyl functionality), ethers, carbonyls, carbonates, carbamates, carbohydrates, non-volatile oxygenates, etc.

In an embodiment where the first mixture's oxygenate comprises ≥90.0 wt. % carbon monoxide based on the weight of the first mixture's oxygenate, the first mixture (i) has a ratio of oxygen atoms to carbon atoms ("O:C")≥0.1, e.g., in the range of 0.1 to 2.0, such as in the range of 0.1 to 0.5, and (ii) comprises 10.0 wt. % to 95.0 wt. % hydrocarbon, e.g., 15.0 wt. % to 85.0 wt. %; 5.0 wt. % to 60.0 wt. % oxygenate. e.g., 10.0 wt. % to 60.0 wt. %; and 0.0 wt. % to 30.0 wt. % molecular hydrogen, e.g., 5.0 wt. % to 25.0 wt. %, the weight percents being based on the weight of the first mixture. The O:C atomic ratio is defined as the ratio of oxygen atoms (as the total number of oxygen atoms in the first mixture) to carbon atoms (as all carbon atoms in the first mixture that are not bound to oxygen atoms, e.g., as can be determined by Nuclear Magnetic Resonance Spectroscopy). For example, the denominator of this ratio can be equal to the number of carbon atoms bound to the first mixture's hydrocarbon. When an oxygenate other than carbon monoxide is utilized, the amount of oxygenate (as defined by the O:C ratio) is equal to (a) the amount of oxygenate that would have been used if the oxygenate were carbon monoxide divided by (b) the Effectiveness Factor corresponding to the oxygenate that is actually used. For example, the first mixture O:C ratio is set equal to (a) divided by (b), where (a) is the O:C ratio that would have been used if the oxygenate were carbon monoxide and (b) is the Effectiveness Factor corresponding to the oxygenate that is actually used. The Effectiveness Factor can be readily determined by one skilled in the art of pyrolysis as the fraction of the first mixture oxygenate oxygen atoms that emerge from pyrolysis as carbon monoxide molecules in the second mixture. The Effectiveness Factors for selected oxygenates is set out in the following table, those Effectiveness Factors being based on exposing a feed comprising methane, molecular hydrogen, and oxygenate, e.g., the first mixture, under a wide range of conditions effective to result in a 50 to 70% conversion of the methane, including peak pyrolysis temperatures ranging from 1400° C. to 1800° C. pressures from 1.3 to 2.0 bar (absolute), and residence times from about 1 to 50 millisecond. It has been found that the Effectiveness Factor, except for that of molecular oxygen, is approximately constant over this broad range, as long as conditions are effective to result in about 50 to 70% hydrocarbon conversion. While not wishing to be bound by any theory or model, it is believed that the variation observed in the Effectiveness Factor of molecular oxygen as a function of pyrolysis conditions results at least in part from the reaction of the molecular oxygen with the first mixture's hydrocarbon, which leads to changes in pyrolysis heat balance. When the oxygenate is a mixture of two or more oxygenates, the mixture's Effectiveness Factor is approximately equal to the linear combination of the individual oxygenate's Effectiveness Factors. For example, when the oxygenate is a mixture of X mole % of carbon monoxide, Y mole % of water, and Z mole % of carbon dioxide, the mixture's Effectiveness Factor=$X \cdot 1.0 + Y \cdot 0.05 + Z \cdot 0.45$. In an embodiment, the Effectiveness Factor is $\geq 0.10$, e.g., $\geq 0.2$, such as $\geq 0.4$. In an embodiment, the oxygenate is one or more of water, molecular oxygen, carbon dioxide, or carbon monoxide. In an embodiment, 90.0 wt. % of the oxygenate (based on the weight of the first mixture's oxygenate) comprises one or more of (i) a lower-cost oxygenate, such as air or water, or (ii) oxygenate such as carbon dioxide, that is naturally present in the hydrocarbon source material.

TABLE

| Oxygenate | Effectiveness Factor |
| --- | --- |
| Carbon Monoxide | 1.0 |
| Water | 0.05 |
| Molecular Oxygen ($O_2$) | 0.15 |
| Carbon Dioxide | 0.45 |
| Methanol | 0.95 |
| Ethanol | 0.65 |

When the first mixture comprises molecular hydrogen, the first mixture optionally has a molecular hydrogen to carbon (as all carbon atoms in the first mixture that are not bound to oxygen atoms, e.g., as can be determined by Nuclear Magnetic Resonance Spectroscopy) molar ratio in the range of from 0.0 to 5.0, e.g., 0.1 to 4.0, such as 1.0 to 3.0 or 1.0 to 2.0. Optionally, the first mixture has a hydrogen (all hydrogen atoms in the first mixture regardless of atomic or molecular form) to carbon (all carbon atoms in the first mixture regardless of atomic or molecular form) atomic ratio in the range of from 1.0 to 15.0, e.g., in the range of from 3.0 to 8.0.

Optionally, the first mixture further comprises diluent, e.g., $\geq 1.0$ wt. % of diluent based on the weight of the first mixture. Suitable diluents (which can be a diluent mixture) include one or more of nitrogen ($N_2$), hydrogen sulfide, $C_{4+}$ mercaptans, amines, mixtures of amines, non-hydrocarbon non-volatiles (whether combustible or not) including refractory inorganics such as refractory oxygenates, inert gas (including inert gas mixtures), etc. In an embodiment, the first mixture comprises $\leq 10.0$ wt. % diluent.

In an embodiment, the first mixture comprises a total amount of non-combustible non-volatiles (e.g., ash, ASTM D-189), from all sources, $\leq 2.0$ parts per million weight (ppmw) based on the weight of the first mixture, e.g., $\leq 1.0$ ppmw. Optionally, the first mixture comprises a total amount of combustible non-volatiles (e.g., tar, asphaltenes, ASTM D-6560) in the first mixture, from all sources, $\leq 5$ wt. % based on the weight of the hydrocarbon in the first mixture, e.g., $\leq 1.0$ wt. %, such as $\leq 100.0$ ppmw or $\leq 10.0$ ppmw, provided the presence of the combustible non-volatiles does not result in $\geq 2.0$ ppmw (e.g. $\geq 1.0$ ppmw) based on the weight of the second mixture.

In an embodiment, at least 15.0 wt. % of the molecular hydrogen in the first mixture (based on the total weight of molecular hydrogen in the first mixture) is molecular hydrogen derived from the second mixture or one or more products thereof. In another embodiment, the first mixture comprises $\geq 50.0$ ppm sulfur based on the weight of the first mixture.

II. Process for Deriving the Second Mixture

The second mixture can be produced by exposing the first mixture under thermal pyrolysis conditions to a temperature $\geq 0.70 \times 10^{3}$ °C., e.g., $\geq 1.20 \times 10^{3}$ °C., such as $\geq 1.40 \times 10^{3}$ °C. The process is illustrated schematically in FIG. 1. The first mixture is derived from one or more source materials 200, the source materials optionally being upgraded in optional preparation stage 204. Optional preparation stage 204 can be utilized for one or more of (i) separating one or more of hydrocarbon, non-combustible nonvolatiles, oxygenate, molecular hydrogen, or diluent from the source material, (ii) adding one or more of hydrocarbon, oxygenate, molecular hydrogen, or diluent to the source material, (iii) thermally upgrading (e.g., coking or visbreaking) the source material, or (iv) catalytically upgrading (e.g., hydroprocessing, such as hydrotreating) the source material, etc. When utilized in connection with one or more of (ii)-(iv), added hydrocarbon, oxygenate, molecular hydrogen, or diluent can be obtained, e.g., from sources external to the process, from byproducts separated from the second or fifth mixtures, etc.

In an embodiment, a first mixture comprising (a) $\geq 1.0$ wt. % oxygenate and (b) $\geq 10.0$ wt. % hydrocarbon is conducted to pyrolysis stage 206, and exposed to a temperature $\geq 1.40 \times 10^{3}$ °C. under pyrolysis conversion conditions, the weight percents being based on the weight of the first mixture. It has been found that this results in an amount of combustible non-volatile hydrocarbon (e.g., coke) in the second mixture in the range of 5.0 wt. % to 40.0 wt. % based on the weight of the second mixture, generally at least part of which is deposited as a residue in the pyrolysis stage. Optionally, at least one of the pyrolysis reactors of stage 206 is a thermal pyrolysis reactor, e.g., a regenerative thermal pyrolysis reactor. In the case of a regenerative reactor, at least a portion of the non-volatile hydrocarbon can be oxidized and conducted away from the pyrolysis stage during regeneration, as discussed in the following sections. At least a portion of the heat derived from this oxidation can be used in. e.g., the pyrolysis reaction for deriving the second mixture from the first mixture.

Preparation stage 204 is optional. In other words, the first mixture can comprise (or consist essentially of, or even consist of) hydrocarbon and oxygenate obtained directly from source materials 200 such as natural gas and air, optionally with no intervening process steps. Following the optional preparation stage 204, the first mixture is conducted to the pyrolysis stage 206 wherein it is exposed to a temperature $\geq 0.70 \times 10^{3}$ °C. under pyrolysis conditions, e.g., thermal pyrolysis conditions, to convert at least a portion of the first mixture to the second mixture. At least a portion of the second mixture, e.g., a portion which comprises $C_2$ unsaturates, hydrogen, and carbon monoxide, is conducted away from the pyrolysis stage to an optional upgrading stage 208, wherein one or more of saturated or unsaturated hydrocarbons (including those containing one or more heteroatoms), diluent, non-volatiles, hydrogen, etc., are separated therefrom. Optionally, the second mixture further comprises a non-volatile portion which can remain in the pyrolysis stage (e.g., in the pyrolysis reactor) e.g., coke. In this embodiment, the third mixture, thus derived from the second mixture by the separations occurring in stages 206 and/or 208, is conducted away from stage 208. In embodiments where, e.g., (i) no portion of the second mixture remains in stage 206 and/or (ii) optional stage 208 is not used, the third mixture comprises, consists essentially of, or even consists of the second mixture. In another embodiment, the third mixture comprises, consists essentially of, or even consists of that portion of the second mixture which is in the vapor phase at the downstream end of the pyrolysis of stage 206.

The third mixture, comprising molecular hydrogen, $C_2$ unsaturates, and CO, is conducted to stage 210 for conversion of at least a portion thereof to a product comprising aldehyde and/or alcohol, e.g., propanal and propanol. For example, catalytic hydroformylation can be used to convert at least a portion of the $C_2$ unsaturates and carbon monoxide in the third mixture, to produce a first product comprising propanal and propanol. In an embodiment, the first product is conducted away from stage 210 to stage 212, where at least a portion of the aldehyde and/or alcohol in the product is converted (e.g., by reduction, catalytic hydrogenation, dehydration, etc.) to a second product comprising olefin, particularly $C_{3+}$ olefin, and more particularly propylene. Conventional hydroformylation and olefin conversion processes are suitable for stages 210 and 212, but the invention is not limited thereto.

The pyrolysis stage 206 will now be described in more detail. While not wishing to be bound by any theory or model, it is believed that exposing the first mixture as defined in Section I to an elevated temperature results in conversion of at least a portion of the first mixture to a second mixture comprising carbon monoxide, ethylene, and ≥1.0 wt. % of acetylene based on the weight of the second mixture, wherein the second mixture has (i) a CO:$C_2$ unsaturates molar ratio in the range of 0.1 to 2.0, such as in the range of 0.15 to 1.2, and (ii) a molecular hydrogen:acetylene molar ratio≥0.75. It is believed that this will occur to at least some extent when the first mixture is exposed to a temperature ≥700° C. The third mixture, and the second mixture from which the third mixture is derived, comprises a stoichiometrically sufficient amount of carbon monoxide and hydrogen to hydroformylate at least a portion of the third mixture's $C_2$ unsaturates to produce a product comprising $C_{3+}$ aldehydes and/or $C_{3+}$ alcohols. In other words, the pyrolysis of stage 206 produces a second mixture comprising $C_2$ unsaturates and sufficient carbon monoxide to allow hydroformylation of at least a portion of the second mixture's $C_2$ unsaturates to $C_{3+}$ aldehydes and $C_{3+}$ alcohols, without producing carbon monoxide in too large an amount as would create gas-handling inefficiencies in stage 208 and stages downstream of stage 208. Although the second mixture can have a CO:$C_2$ unsaturates molar ratio≤20.0, a molar ratio >2.0 can result in the production of more CO than is needed for the hydroformylation, which can be undesirable. In an embodiment, the first mixture has an STP enthalpy $H_i$ and the second mixture has an STP enthalpy $H_o$, wherein $H_o$–$H_i$≥0.0 kcal per mole of hydrocarbon in the first mixture. The term "STP" means Standard Temperature and Pressure, i.e., a temperature of 0° C. and a pressure of 100 kPa (absolute). Optionally, the first mixture comprises methane and $H_o$–$H_i$≥10.0 kcal per mole of hydrocarbon in the first mixture.

Conventional pyrolysis reactors are suitable for use in stage 206, but the invention is not limited thereto. Suitable reactors include, for example, regenerative, reverse-flow reactors as described in U.S. Patent App. Pub. No. 2007/0191664 and thermal pyrolysis reactors as described in U.S. Pat. No. 7,491,250; U.S. Patent Application Ser. No. 61/349,464; and U.S. Patent App. Pub. Nos. 2007/0144940 and 2008/0142409, all of which are incorporated by reference herein in their entirety. Optionally, the thermal pyrolysis is conducted under high-severity thermal pyrolysis conditions, e.g., by exposing the first mixture to a temperature ≥1.30×10³° C. or ≥1.40×10³° C., such as in the range of about 1.30×10³° C. to about 2.30×10³° C., e.g., in the range of about 1.45×10³° C. to about 1.80×10³° C. In an embodiment where the reactor's temperature is relatively constant over the reaction region, as may be the case when the pyrolysis reactor is a tubular reactor heated by a burner located in proximity to the outside of the tube, the first mixture achieves a peak pyrolysis gas temperature in the range of about 1.50×10³° C. to about 1.675×10³° C., e.g., in the range of about 1.54×10³° C. to about 1.65×10³° C. Should the reactor's temperature exhibit significant variation over the reaction region, as may be the case in a regenerative, reverse-flow pyrolysis reactor, the first mixture can achieve a peak pyrolysis gas temperature in the range of about 1.40×10³° C. to about 2.20×10³° C., e.g., in the range of about 1.45×10³° C. to about 1.80×10³° C.

Generally, ≥25.0 wt. % (such as ≥50.0 wt. % or ≥75.0 wt. %) of the first mixture achieves a peak pyrolysis gas temperature ≥1.40×10³° C., e.g., in the range of about 1.50×10³° C. to about 1.675×10³° C., the weight percents being based on the weight of the first mixture.

The peak pyrolysis gas temperature can be regulated to produce the desired carbon monoxide:$C_2$ unsaturates molar ratio and acetylene:ethylene molar ratio in the second and third mixtures, e.g., into a range that optimizes the amount of aldehyde and/or alcohol produced in stage 210. For example, it is observed that exposing the first mixture to a peak pyrolysis gas temperature ≥1.54×10³° C. increases the relative amount of carbon monoxide in the second mixture and decreases the amount of that portion of the non-volatiles in the second mixture as are produced by the pyrolysis. Stage 206 generally operates at a total pressure ≥10.0 mbar (absolute), e.g., in the range of 0.10 bar to 25.0 bar, such as 1.0 bar to 20.0 bar, or 2.0 bar to 7.0 bar.

Although the process is robust and can operate within a wide range of pyrolysis conditions, e.g., temperature, pressure, residence times, severity, etc., the conditions are generally selected to increase the relative amount of $C_2$ unsaturates in the second mixture. e.g., to increase the acetylene to $C_{3+}$ weight ratio. Relatively long residence times can result in over-cracking of the feed molecules, leading to an undesirable increase in the amount of methane and/or $C_{3+}$ in the second mixture. In an embodiment, residence time is ≤ about 0.3 seconds, e.g., ≤0.05 seconds. In an embodiment, the pyrolysis is high-severity, thermal pyrolysis and the residence time is ≤0.05 seconds, such as ≤0.02 seconds. Residence time can be selected, e.g., for optimum $C_2$ unsaturates yield under pyrolysis conditions. This can be done by measuring the amount of $C_2$ unsaturates in the second mixture under substantially constant thermal pyrolysis conditions at a plurality of residence times. The optimum residence time can be approximated using conventional interpolation and extrapolation of the measured values. The optimum residence time can also be approximated using pyrolysis reaction simulations of second mixture composition as a function of pyrolysis conditions and residence time, including conventional pyrolysis reaction simulations.

A third mixture, derived from at least a portion of the second mixture, is conducted to a conversion stage 210 for converting at least a portion of the carbon monoxide and $C_2$ unsaturates therein to a first product comprising aldehyde and/or alcohol, e.g., propanal and/or propanol. The third mixture can be derived from the second mixture by way of an optional upgrading stage 208, which will now be described in more detail.

If desired, stage 208 can include upgrading means, e.g., means for removing from the second mixture one or more of saturated or unsaturated hydrocarbon (including those containing one or more heteroatoms), diluent, non-volatiles, hydrogen, etc. For example, stage 208 can include one or more of a tar and/or solid removal means, compression means, adsorption and/or absorption means, distillation means, washing means, or drying means. While stage 208 can encompass conventional processing, e.g., conventional dividing, conversion, and/or separation means, the invention is not limited thereto. Separation means can be used, e.g., for removing condensable species (e.g., condensable hydrocarbon) from the second mixture. Such condensable species may include vaporized liquids that condense, such as benzene, or those that can be separated via, e.g., cooled separations for example, adsorption, vapor liquid separators, flash drums, etc. Suitable separations means include conventional distillation or refrigerated distillation means such as one or more of demethanators and $C_2$ splitters, etc., but the invention is not limited thereto. The invention is compatible with low-pressure demethanizers and high-pressure demethanizers (e.g., those operating at a pressure ≥3.5 MPa). Stage 208 can include contacting the second mixture or a portion thereof with a fluid having a pH>7.0. Acetylene can be separated from the second mixture, e.g., utilizing separations means such as by contacting the second mixture with a polar fluid such as one or more of furfural, phenol, n-methyl-2-pyrrolidone, methanol, acetone or tetrahydrofuran. Suitable polar fluids are disclosed in U.S. Pat. Nos. 3,093,697; 3,617,495; 4,274,841; and 7,045,670, which are incorporated by reference herein in their entirety. Acetylene separated from the second mixture can be conducted away from stage 208, e.g., for storage or further processing such as converting at least a portion of the separated acetylene to ethylene. Conventional acetylene conversion processes can be utilized to do this, including gas-phase and/or liquid phase acetylene conversion processes, but the invention is not limited thereto. It has been observed that some acetylene conversion catalysts have an increase in selectivity for ethylene in the presence of carbon monoxide, e.g., when the acetylene converter's feed has a carbon monoxide:acetylene molar ratio in the range of about $3.5 \times 10^{-3}$ to 0.20. In one embodiment, carbon monoxide and acetylene are separated from the second mixture, with the acetylene being converted to ethylene in the presence of a catalyst having an increased selectivity for ethylene in the presence of the carbon monoxide; the carbon monoxide: acetylene molar ratio being in the range of about $3.5 \times 10^{-3}$ to 0.20.

If desired, at least a portion of any light-gas in the second mixture (e.g., one or more of molecular hydrogen, light saturated hydrocarbon such as methane, carbon dioxide, hydrogen sulfide, etc.) can be removed in stage 208. Suitable light-gas removal means include one or more of separation, basic wash (e.g., caustic wash or amine scrubbing), or drying etc. Optionally, the separation means includes one or more of pressure swing adsorption, membranes and/or cryogenic distillation, electrochemical separation, or liquid absorption. Light-gas separation means may be used to separate hydrogen, carbon monoxide, methane, nitrogen or other light gases. Optionally, the removed light gas can be used. e.g., to adjust the stoichiometry of the first or fourth mixtures (e.g., by increasing the hydrogen and/or diluent content, etc.), as a stripping medium (e.g., for upgrading one or more sources from which the first mixture is derived, such as by stripping upstream of stage 206, e.g., in stage 204), etc. For example, should the second mixture contain more hydrogen than is needed for hydroformylation, at least a portion of the hydrogen in the second mixture can be removed, e.g., by partially cooling the second mixture (optionally at essentially constant pressure) to condense at least a portion of the second mixture and then separating therefrom a vapor comprising hydrogen. The separated hydrogen can be conducted away and utilized, e.g., for producing the first and/or fourth mixtures and/or for converting to ethylene at least a portion of any acetylene separated from the second mixture.

Optionally, stage 208 includes means for removing at least a portion of any water present in the second mixture, e.g., by one or more of a methanol treatment, such as those described in Belgian Patent No. 722,895, adsorption, extraction by diethylene glycol, etc. For example, stage 208 can include one or more driers located, e.g., downstream of caustic treatment, for removing at least a portion of the water, including conventional driers, e.g., molecular sieve dryers.

When it is desirable for the third mixture to have a higher pressure and/or lower temperature than the second mixture, stage 208 can include, e.g., means for cooling and then compressing the portion of the second mixture conducted away from stage 206 in order to produce the third mixture. For example, in embodiments where stage 206 has an outlet pressure that is less than the inlet pressure of hydroformylation stage 210, stage 208 can include, e.g., compressing at least the portion of the second mixture from which the third mixture is derived in order to achieve the desired stage 210 inlet pressure. Should the second mixture comprise acid gases (e.g., $CO_2$ and/or $H_2S$), these can be removed, e.g., downstream of the compression—a desirable location since the gas volume has been reduced significantly during compression. Conventional methods are suitable for removing acid gases, e.g., caustic treatment, but the invention is not limited thereto. Acid gases separated from the second mixture can be conducted away, e.g., for storage or further processing such as in a Claus plant.

Stage 208 can be utilized to produce the third mixture by combining at least a portion of the second mixture with added species, such as molecules obtained from other stages of the process. For example, at least a portion of the product of the hydroformylation of stage 210 can be separated and conducted upstream of stage 210 (and/or upstream of one or more conversion zones thereof when more than one conversion zone is utilized). e.g., to stage 208 to increase the amount of carbon monoxide and/or molecular hydrogen in the third mixture. In other words, in one embodiment the third mixture comprises a portion of the second mixture to be conducted to the hydroformylation stage 210 and further comprises one or more of acetylene, ethylene, methane, ethane, carbon monoxide, or molecular hydrogen recycled, e.g., from downstream of stage 210. Stage 208 can include means for separating carbon monoxide from the second mixture, all or a portion of which can be utilized to increase the third mixture's carbon monoxide content. This might occur when low-temperature separations are utilized to remove undesired low-boiling point species from the second mixture. Carbon monoxide can then be recovered from among such low-boiling species and returned to the process, e.g., to bring the third mixture's carbon monoxide to $C_2$ unsaturates molar ratio into the desired range.

In an embodiment, at least a portion of the molecular hydrogen, hydrocarbon, diluent, etc., separated from the second mixture in upgrading stage 208 is recycled, e.g., by combining such separated species with one or more of the first mixture's source materials, e.g., in preparation stage 204. The second mixture and third mixture will now be described in more detail.

III. The Second and Third Mixtures

When a first mixture as specified in Section I is exposed to a temperature ≥700° C. under thermal pyrolysis conditions, the second mixture generally comprises molecular hydrogen, carbon monoxide, and ≥1.0 wt. % of $C_2$ unsaturates based on the weight of the second mixture, the second mixture having a $CO:C_2$ unsaturates molar ratio in the range of 0.10 to 2.0. Optionally, the second mixture comprises $C_2$ unsaturates in an amount $A_1$ (wt. % based on the weight of the second mixture) and further comprises $C_{3+}$ hydrocarbon in an amount $A_2$ (wt. %, based on the weight of the second mixture). Optionally, the second mixture has a ratio of $A_2$ to $A_1$ of ≤ about 1.0, e.g., ≤ about 0.4, such as ≤ about 0.3. Optionally, the second mixture has one or more of the following additional properties: an acetylene:ethylene molar ratio≥0.0, such as in the range of about 0.5 to about 20.0, e.g., about 1.20 to about 10.0, or about 2.0 to about 10.0; a molecular hydrogen: $C_2$ unsaturates molar ratio in the range of 2.0 to 20.0; a molecular hydrogen:acetylene molar ratio≥0.75, or ≥3.0, e.g., in the range of 3.0 to 20.0; a carbon monoxide:$C_2$ unsaturates molar ratio in the range of 0.15 to 2.0. e.g., in the range of 0.15 to 1.2; a water content≤50.0 wt. % based on the weight of the second mixture, e.g., ≤25.0 wt. %, such as ≤10.0 wt. %; or a carbon dioxide:$C_2$ unsaturates molar ratio≤1.0, e.g., ≤0.30. Optionally, the second mixture comprises ≥1.0 wt. %, methane e.g., 2.0 wt. % to 50.0 wt. %; ≥1.0 wt. % carbon monoxide, e.g., 2.0 wt. % to 50.0 wt. %, such as 5.0 wt. % to 35.0 wt. %; ≥1.0 wt. % molecular hydrogen, e.g., 2.0 wt. % to 50.0 wt. %; ≥1.0 wt. % acetylene, e.g., 2.0 wt. % to 40.0 wt. %; ≥1.0 wt. % ethylene, e.g., 2.0 wt. % to 70.0 wt. %, such as 2.0 wt. % to 20.0 wt. %; and ≥1.0 wt. % $C_{3+}$, e.g., 2.0 wt. % to 50.0 wt. %, the weight percents being based on the weight of the second mixture.

The third mixture can be derived from the second mixture in one or more upgrading/treatment stages, e.g., by separating from the second mixture one or more of hydrogen, saturated hydrocarbon, unsaturated hydrocarbon (e.g., acetylene), oxygenate, diluent, etc. The third mixture can comprise, consist essentially of, or consist of the second mixture, e.g., that part of the second mixture which is in the vapor phase at the downstream end of the most-downstream pyrolysis reactor of stage 206.

In an embodiment, the third mixture comprises carbon monoxide and ≥1.0 wt. % of $C_2$ unsaturates based on the weight of the third mixture, the third mixture having a $CO:C_2$ unsaturates molar ratio in the range of 0.1 to 2.0. Optionally, the balance of the third mixture (to equal 100.0 wt. %) comprises molecular hydrogen and/or diluent.

Optionally, the third mixture is substantially free of $C_{3+}$, e.g., $C_{3+}$ hydrocarbon. For example, the third mixture can comprise $C_{3+}$ hydrocarbon in an amount ≤1.0 wt. %, e.g., ≤0.01 wt. % based on the weight of the third mixture. Optionally, the third mixture has one or more of the following additional properties: an acetylene:ethylene molar ratio≤20.0, or in the range of about 0.0 to about 20.0, about 0.1 to about 10.0, such as about 1.0 to about 10.0; a molecular hydrogen: $C_2$ unsaturates molar ratio≥2.0, e.g., in the range of 2.0 to 10.0; a molecular hydrogen:acetylene molar ratio≥0.75, or ≥3.0, e.g., in the range of 3.0 to 20.0; a molecular hydrogen:ethylene molar ratio≥1.0, e.g., in the range of 1.0 to 20.0; or a molar ratio of molecular hydrogen to carbon monoxide≥1.0, e.g., in the range of from about 1.0 to about 100.0, such as in the range of from about 1.0 to about 10.0, or in the range of about 2.0 to about 5.0.

Optionally, the mole percents of carbon monoxide, molecular hydrogen, and $C_2$ unsaturates in the third mixture are in the following ranges: carbon monoxide in the range of from about 1.0 mole % to 50.0 mole %, such as from about 1.0 mole % to 35 mole %; molecular hydrogen in the range of from about 1.0 mole % to 98.0 mole %, e.g., about 2.0 mole % to about 95.0 mole %, such as about 10.0 mole % to 80.0 mole %; and $C_2$ unsaturates in the range of from about 0.1 mole % to 35.0 mole %, such as from about 1.0 mole % to 35.0 mole %, the mole percents being based on the number of moles of carbon monoxide, molecular hydrogen, and $C_2$ unsaturates per mole of the third mixture.

The third mixture generally has an amount of carbon monoxide and molecular hydrogen with respect to the amount of ethylene and acetylene that is substantially a stoichiometric amount for converting ≥90.0 wt. % of the third mixture's $C_2$ unsaturates (e.g., ≥95.0 wt. %, such as ≥99.0 wt. %) to $C_{3+}$ aldehyde and/or $C_{3+}$ alcohol (e.g., propanal and/or propanol) based on the weight of the third mixture. In this regard, a substantially stoichiometric conversion of these species means that per mole of the third mixture (i) the number of moles of carbon monoxide is substantially equal to the sum of the number of moles of acetylene and ethylene; and (ii) the number of moles of molecular hydrogen per mole of the third mixture is substantially equal to the sum of the number of moles of ethylene plus twice the number of moles of acetylene. Optionally, the third mixture comprises 0.0 wt. % to 50.0 wt. % acetylene (such as 0.1 wt. % to 10.0 wt. %), 0.0 wt. % to 50.0 wt. % ethylene, 1.0 wt. % to 60.0 wt. % carbon monoxide, and 0.1 wt. % to 30.0 wt. % molecular hydrogen, with the amount of molecular hydrogen being in the range from 0.5 to 10.0 times the stoichiometric amount for converting to $C_{3+}$ aldehyde and/or $C_{3+}$ alcohol≥90.0 wt. % of the third mixture's $C_2$ unsaturates (e.g., ≥ about 95.0 wt. % such as ≥ about 99.0 wt. %) based on the weight of the third mixture; e.g., in the range from about 1.0 to about 5.0 times the stoichiometric amount to convert ≥ about 90.0 wt. % of the $C_2$ unsaturates to propanal and/or propanol (e.g., ≥ about 95.0 wt. % such as ≥ about 99.0 wt. %) based on the weight of the third mixture. Optionally, the amount of carbon monoxide in the third mixture is in the range of from about 0.5 to about 2.0 times the stoichiometric amount for converting ≥90.0 wt. % of the third mixture's $C_2$ unsaturates to propanal or propanol (e.g., ≥ about 95.0 wt. % such as ≥ about 99.0 wt. %) based on the weight of the third mixture. In an embodiment, the third mixture is converted (in stage 210) to produce a product (the "first product") comprising aldehyde and alcohol. An example of one such conversion process will now be described in more detail. The invention is not limited to this conversion process, and the following description is not meant to foreclose other conversion processes within the broader scope of the invention.

IV. Process for Deriving the First-Fourth Products

As shown in FIG. 1, a first mixture, optionally derived from one or more source materials in pretreatment stage 204, is conducted to stage 206 for pyrolysis. A vapor-phase portion of the second mixture derived from the first mixture by the pyrolysis is conducted away from stage 206. A third mixture is subjected to hydroformylation in stage 210 to produce a first product comprising $C_{3+}$ aldehyde and/or $C_{3+}$ alcohol, the third mixture being either substantially the same as the second mixture or derived therefrom in optional stage 208. An optional separations stage 211 can be utilized for separating from the first product at least a portion of the $C_{3+}$ aldehyde and/or $C_{3+}$ alcohol therein, with at least a portion of the separated $C_{3+}$ aldehyde and/or $C_{3+}$ alcohol being converted in optional conversion stage 212 to a second product comprising olefin, e.g., propylene. As shown in FIG. 1, Stage 208 can include means for extracting acetylene from the second mixture, thereby decreasing the amount of acetylene in the third mixture. The extracted acetylene can be conducted to optional acetylene conversion stage 215. A third product comprising ethylene can be separated from the effluent of stage 215 by optional separations stage 216. Optional separations stage 211 can also be utilized for separating $C_2$ unsaturates, such as acetylene, and optionally carbon monoxide, molecular hydrogen, and saturated hydrocarbon from the first product, one or more of these being conducted to optional conversion stage 217 for producing a fourth product comprising, e.g., ethylene as shown in FIG. 1. Alternatively, stage 217 can be located downstream of stage 212, for converting $C_2$ unsaturates in the stage 210 effluent in the presence of the aldehyde and/or alcohol, as shown in FIG. 2c. Stages 215 and 217 can utilize conventional acetylene conversion methods, including those with increased selectivity for ethylene in the presence of carbon monoxide. Stages 204 and 208 can utilize conventional separations, extraction, and upgrading methods as described in the preceding sections. Stages 211 and 216 can utilize conventional separations methods. The invention is not limited to such conventional methods. Selected embodiments will now be described in more detail. The invention is not limited to these embodiments, and this description is not meant to foreclose other embodiments within the broader scope of the invention.

Figure 2A:
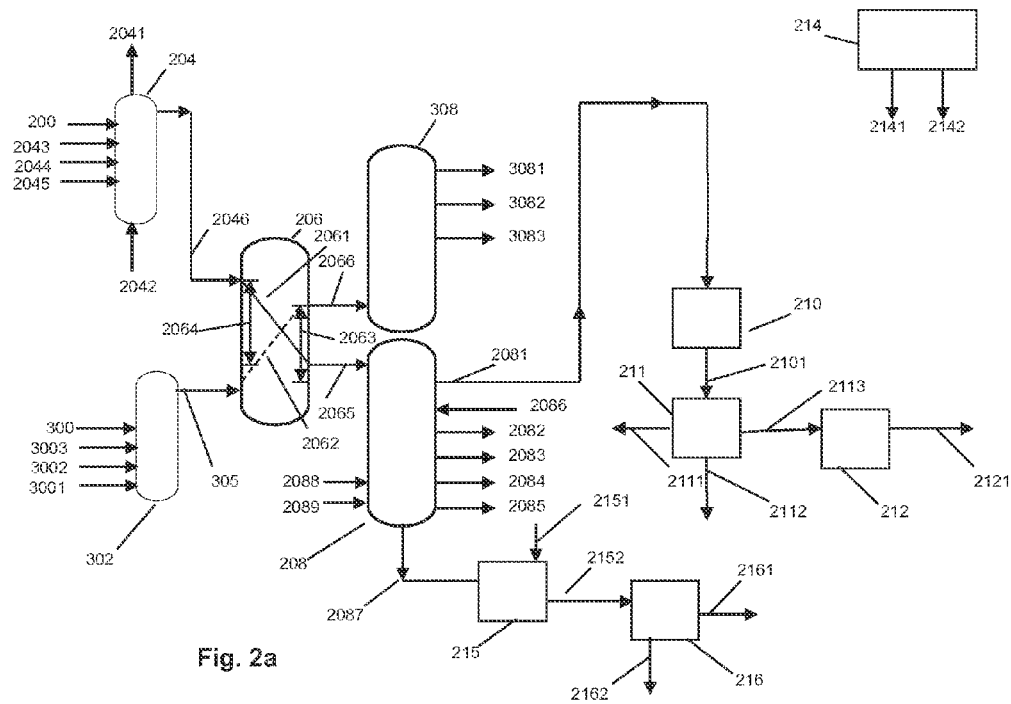
FIG. 2a schematically illustrates an embodiment of the invention utilizing a reverse-flow pyrolysis reactor.
Figure 2B:
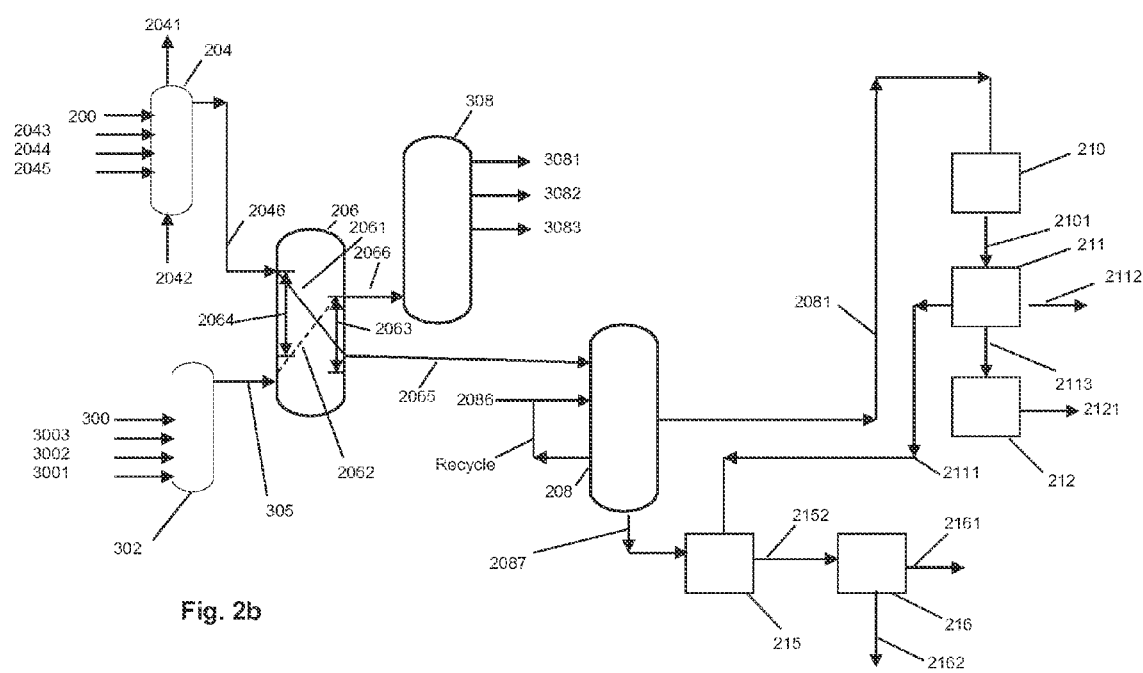
FIG. 2b illustrates another embodiment of the invention utilizing a reverse-flow pyrolysis reactor. The figure shows optional recycle of a polar fluid within optional upgrading stage 208, and the transfer of one or more of $C_2$ unsaturates, saturated hydrocarbon, carbon monoxide or molecular hydrogen from optional separation stage 211 via conduit 2111 to optional conversion stage 215.
Figure 2C:
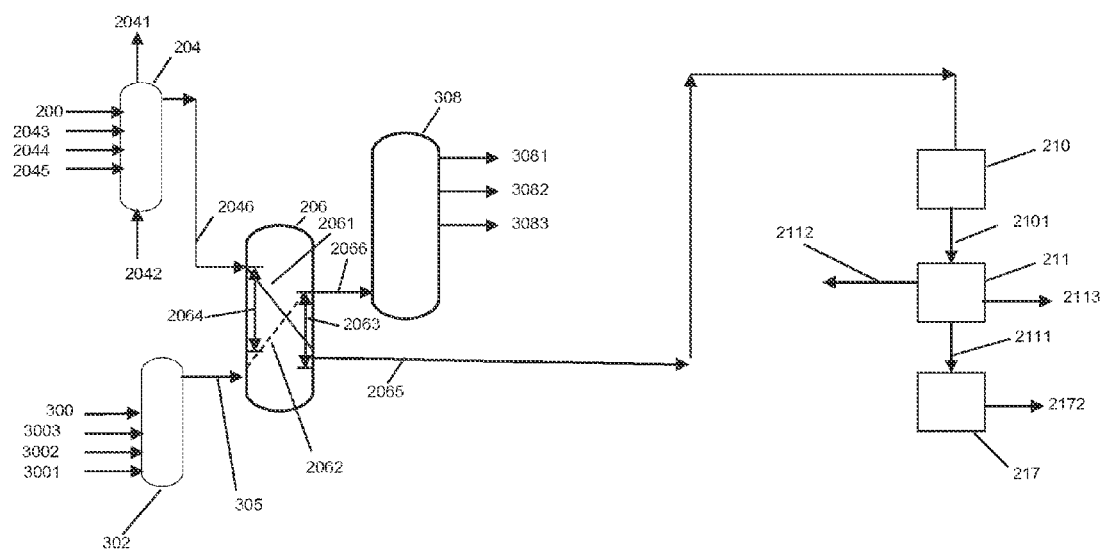
FIG. 2c illustrates yet another embodiment of the invention utilizing a reverse-flow pyrolysis reactor. The figure shows conduit 2065 transferring at least a portion of the second mixture directly from stage 206 to conversion stage 210. Except as expressly noted herein, reference numbers in FIGS. 2a-2c refer to the same components.

The third mixture can be conducted to conversion stage 210 for converting at least a portion thereof to a first product comprising $C_3$ aldehyde and/or $C_{3+}$ alcohol, such as propanal and/or propanol, either directly (e.g., with no intervening steps as shown in FIG. 2c) or after first being subjected to one or more separation/upgrading operations, e.g., in optional stage 208 (as shown in FIGS. 2a and 2b). For example, in one embodiment, the third mixture comprises, consists essentially of, or even consists of the vapor-phase effluent of pyrolysis stage 206, which is conducted to the conversion of stage 210 with no intervening steps, e.g., with no intervening chemical conversion steps. This embodiment can be particularly beneficial when the third mixture contains more carbon monoxide and/or hydrogen than is needed for hydroformylating the third mixture's $C_2$ unsaturates. In this case, the acetylene converter of optional stage 217 can utilize (i) the excess molecular hydrogen for acetylene hydrogenation and (ii) the excess carbon monoxide for increasing the converter's ethylene selectivity. In another embodiment, the third mixture comprises, consists essentially of, or consists of a portion of the vapor-phase effluent of pyrolysis stage 206, the portion having substantially the same composition as such vapor-phase effluent and being divided therefrom in stage 208, e.g., by a splitter. As used herein the term "chemical conversion" of a composition means the chemical transformation of at least 0.10 moles/second of the composition, excluding physical transformations such as phase changes, temperature changes, pressure changes, separations, etc.

In other embodiments, the second and third mixtures have substantially different compositions, such as when the third mixture is derived from the vapor-phase portion of the second mixture in stage 208 by one or more separation, addition, or chemical conversion. For example, in one embodiment the third mixture is obtained by dividing the vapor-phase effluent of pyrolysis stage 206 to produce first and second streams (e.g., using a splitter), hydrogenating in stage 208 at least a portion of the first stream's acetylene to produce ethylene, and then utilizing at least a portion of the ethylene to produce the third mixture. The second stream can be conducted away from stage 208, e.g., for conversion of at least a portion of the second stream's acetylene to ethylene in optional stage 215. In another embodiment, acetylene is extracted from the vapor-phase portion of the second mixture in stage 208, e.g., using a polar fluid, with (i) at least a portion of the acetylene-lean raffinate being utilized to produce the third mixture, and optionally (ii) at least a portion of the acetylene-rich extract being conducted away from stage 208, such as for conversion of at least a portion of the extract's acetylene to ethylene in optional stage 215. The polar fluid can remove, e.g., ≥50.0 wt. %, e.g., ≥90.0 wt. %, such as ≥95.0 wt. % of the second mixture's acetylene, based on the weight of the second mixture's acetylene. Stage 208, when used, may have two broad functions. The first function is to remove poisons, impurities (e.g., hydrogen sulfide), or excess species (e.g., molecular hydrogen) that are not needed by downstream conversion, and the second function is to direct by splitting or separation the flows of downstream reactants (e.g., $C_2$ unsaturates, carbon monoxide, and/or molecular hydrogen) to designated conversion locations (e.g., 210, 215). The functions may be effected in any order, may be effected by single or multiple process steps. The first function may be applied even when no division of the downstream reactants is made (as in FIG. 2c), and/or prior to or after the splitting and separating of downstream reactants described in FIGS. 2a and 2b. Selected embodiments of stage 210 will now be described in more detail.

At least a portion of the pyrolysis product of stage 206 (such as the second mixture or a third mixture derived from the second mixture, e.g., by separation) is conducted to hydroformylation stage 210, the third mixture comprising molecular hydrogen, carbon monoxide, and ≥1.0 wt. % of $C_2$ unsaturates based on the weight of the third mixture, wherein the third mixture has a $CO:C_2$ unsaturates molar ratio in the range of 0.1 to 2.0. Conventional hydroformylation processes are suitable, but the invention is not limited thereto, and the following description is not meant to foreclose other hydroformylation processes within the broader scope of the invention. Such processes include, e.g., the OXO process, and those described in U.S. Pat. Nos. 1,134,677; 5,856,592; and 6,049,011; all of which are incorporated by reference herein in their entirety. Representative conventional hydroformylation processes utilizing a catalytically effective amount of a hydroformylation catalyst can operate under one or more of the following process conditions: (i) temperature in the range of 50.0° C. to 200.0° C. (e.g., 80.0° C. to 180.0° C., such as 85.0° C. to 155° C.); total pressure in the range of ≤50.0 mPa (e.g., ≤5.0 MPa [absolute], such as in the range of 0.05 mPa to 5.0 MPa); and (iii) carbon monoxide pressure≤50.0% of the total pressure. Optionally, the total pressure is ≤25.0 MPa.

The hydroformylation of stage 210 can be conducted in batch mode, continuously, semi-continuously, or combinations thereof. When operated continuously, superficial velocities in the range of from, e.g., about 1.50 to about 61.0 cm/sec (0.05 to 2.00 ft/sec), such as from about 3.0 to about 30.0 cm/sec (0.10 to 1.00 ft/sec) can be used, though this is not critical.

Such processes can be carried out in the liquid phase using a hydroformylation catalyst comprising one or more elements of Group VIII of the Periodic Table of the Elements, e.g., Co, Fe, Ni, Rh, Ru, and Ir; such as Rh. In an embodiment, the hydroformylation catalyst is derived from a complex of Rh and an organic phosphorus composition, such as (HRh $(CO)_x(PPh_3)_y$; (x+y=4), e.g., $HRh(CO)(PPh_3)_3$. Suitable hydroformylation processes are described, e.g., in U.S. Pat. No. 5,675,041, which is incorporated by reference herein in its entirety. Since the third mixture can comprise ethylene and acetylene, it is desirable for the hydroformylation catalyst to have significant activity for the hydroformylation of both acetylene and ethylene. In embodiments where the selected hydroformylation catalyst loses significant activity, e.g., when the third mixture's acetylene:ethylene molar ratio is too large, the acetylene content in the portion of the second mixture from which the third mixture is derived can be lowered, e.g., by (i) separating acetylene from the second mixture, e.g., in stage 208, and/or (ii) converting at least a portion of the second mixture's acetylene to ethylene in an optional stage (not shown). In other embodiments, the hydroformylation of stage 210 converts substantially all of the third mixture's acetylene to propanal and/or propanol before converting a significant amount of the third mixture's ethylene. For hydroformylation catalyst having significant activity for converting acetylene and/or ethylene only, species such as molecular hydrogen, saturated hydrocarbon, carbon monoxide, and other species that are not catalyst poisons can be considered as diluent. Since propanal and propanol have an atmospheric boiling point that is significantly greater than the boiling point of diluent species typically present in the second and third mixtures, the propanal and propanol are readily separated from the first product by separation. e.g., conventional separation such as distillation, stripping, or flashing. When homogeneous catalysis is used. e.g., as in the hydroformylation of U.S. Pat. No. 5,675,041, the process can include means for separating the hydroformylation catalyst from the first product.

The first product generally comprises ≥1.0 wt. % $C_{3+}$ aldehyde and/or ≥1.0 wt. % $C_{3+}$ alcohol based on the weight of the first product, e.g., ≥1.0 wt. % propanal and/or ≥1.0 wt. % propanol, such as ≥25.0 wt. % of propanal and/or propanol. Optionally, the first product further comprises ≤10.0 wt. % of molecular hydrogen, ≥1.0 wt. % of carbon monoxide, ≤1.0 wt. % of ethylene, and ≤1.0 wt. % of diluent, the weight percents being based on the weight of the first product. Optionally, the first product comprises about 5.0 wt. % to about 50.0 wt. % propanal and about 0.1 wt. % to about 50.0 wt. % propanol based on the weight of the first product.

If desired, the process can further comprise deriving from at least a portion of the first product a second product comprising olefin. For example, at least a portion of the first product is conducted to stage 212 where it can be subjected to a process (the "olefin conversion process") for converting at least a portion of the aldehyde and alcohol in the first product to the second product. An example of one such conversion process will now be described in more detail. The invention is not limited to this conversion process, and the following description is not meant to foreclose other conversion processes within the broader scope of the invention.

At least a portion of the first product can be converted in stage 212 to a second product, wherein the first product comprises aldehyde and alcohol and the second product comprises olefin. For example, in one embodiment the first product is conducted from stage 210 to olefin conversion stage 212 with no intervening steps. In another embodiment, the first product is conducted from stage 210 to olefin conversion stage 212 with no intervening chemical conversion steps. In this case, the first product can be conducted to separations stage 211, as shown in FIG. 1, where one or more of $C_2$ unsaturates, molecular hydrogen, saturated hydrocarbon, or carbon monoxide are separated from the aldehyde and/or alcohol upstream of stage 212. In yet another embodiment, at least a portion of the first product is chemically converted upstream of stage 212, e.g., by chemically converting at least a portion of the aldehyde in the first product to alcohol. The conversion of stage 212 can comprise, e.g., one or more conventional processes for converting aldehyde and alcohol to olefin, such as one or more reducing and/or dehydration processes, though the invention is not limited thereto, and the following description is not meant to foreclose other methods for converting aldehydes and alcohols to olefins within the broader scope of the invention. One suitable conventional method is described in U.S. Pat. No. 6,121,503, which is incorporated by reference herein in its entirety. In another embodiment, stage 212 is utilized to convert $C_{3+}$ aldehyde in the first product to alcohols, such as branched $C_9$ alcohols and esters thereof. In such an embodiment, stage 212 can include one or more processes for aldol condensation from propanal, e.g., those described in U.S. Pat. No. 6,307,093, which is incorporated by reference herein in its entirety.

In an embodiment, a first portion of the first product is subjected to the olefin conversion in conversion stage 212. The first portion can comprise, e.g., ≥25.0 wt. %, such as ≥50.0 wt. %, or ≥75.0 wt. %, or ≥90.0 wt. % of the first product, based on the weight of the first product. Optionally, the first portion further comprises diluent. The diluent can comprise, e.g., one or more of (i) non-aldehyde, non-alcohol oxygenate such as carbon monoxide, carbon dioxide, water, dimethyl ether, diethyl ether, methyl mercaptan, dimethylketone, etc., and mixtures thereof; (ii) inorganic materials such as helium, argon, nitrogen, hydrogen, etc, and mixtures thereof; or (iii) one or more hydrocarbon such as paraffins, olefins, aromatics, etc., and mixtures thereof. Optionally, the first portion has an (aldehyde+alcohol):diluent molar ratio in the range of about 1:1 to about 1:4. In an embodiment, the diluent is water. When the desired diluent species and relative amounts are not present in the first portion, all or a portion of the desired diluent (which can be a diluent mixture) can be added to the first portion from, e.g., one or more sources external to the process.

In an embodiment, the catalyst utilized in stage 212 for converting the first portion of the first product to olefin comprises a catalytically effective amount of at least one molecular sieve, e.g., zeolite (e.g., one or more of ZSM-5, ZSM-48, Fe-ZSM-5, etc.) and/or silicoaluminophosphate (e.g., SAPO-34). The catalysts described in U.S. Pat. No. 6,121,503 can be used, for example.

The conversion of stage 212 can be carried out at catalytic conversion process conditions including a pressure in the range of about 0.001 atmospheres (0.76 torr) to about 1000 atmospheres (760,000 torr), such as about 0.01 atmospheres (7.6 torr) to about 100 atmospheres (76,000 torr); a temperature in the range of from about 350° C. (662° F.) to about 550° C. (1022° F.), e.g., from about 450° C. (842° F.) to about 550° C. (1022° F.), such as about 440° C. (824° F.) to about 460° C. (860° F.); and a space velocity (feed:catalsyt on a weight basis. i.e., WHSV) in the range of about 0.01 per hour to about 100 per hour, e.g., about 0.5 per hour to about 10 per hour, such as about 0.8 per hour to about 1.2 per hour. In an embodiment, the catalyst and process conditions of stage 212 are selected to provide an amount of aldehyde and alcohol conversion to olefin in the range of about 98.0% to 100.0% on a molar basis. The process conditions described in U.S. Pat. No. 6,121,503 can be used, for example. A second product is conducted away from stage 212, the second product comprising olefin and being derived from the first product.

In an embodiment, the second product comprises ≥ about 1.0 wt. % of olefin, e.g., ≥10.0 wt. % of olefin, such as ≥50.0 wt. % of olefin, based on the weight of the second product. Optionally, the second product comprises ≥ about 1.0 wt. % of propylene, e.g., ≥10.0 wt. % of propylene, such as ≥25.0 wt. % of propylene, based on the weight of the second product. Optionally, at least a portion of the second product is polymerized to form a fourth product comprising, e.g., polypropylene. Conventional polymerization process can be used, including those utilizing one or more comonomers with the propylene, but the invention is not limited thereto.

In one or more embodiments, the process utilizes a reverse-flow, regenerative pyrolysis reactor system for at least a portion of the pyrolysis of stage 206. An example of such a process within the scope of the invention will now be described in more detail. The following description is not meant to foreclose other embodiments within the broader scope of the invention.

V. Particular Embodiment Utilizing a Reverse-Flow. Regenerative Pyrolysis Reactor In one or more embodiments, the invention relates to a hydrocarbon conversion system and process, comprising exposing a first mixture comprising ≥1.0 wt. % of hydrocarbon and ≥1.0 wt. % of oxygenate based on the weight of the first mixture to a temperature ≥$1.4 \times 10^{3}$° C. at a total pressure ≥0.1 bar (absolute) under thermal pyrolysis conditions in a first region of a reverse-flow, regenerative pyrolysis reactor and conducting away from the first region at least a portion of a second mixture, the second mixture being derived from the first mixture, wherein (i) the second mixture comprises molecular hydrogen, carbon monoxide, and ≥1.0 wt. % of $C_2$ unsaturates based on the weight of the second mixture (and optionally ≥1.0 wt. % of acetylene based on the weight of the second mixture) and (ii) the second mixture has a carbon monoxide:$C_2$ unsaturates molar ratio in the range of 0.10 to 2.0 and a carbon dioxide:$C_2$ unsaturates molar ratio≤0.30. The process for deriving the second mixture from the first mixture is generally endothermic, and can be conducted, e.g., under high-severity thermal pyrolysis conditions. The process further comprises converting at least a portion of a third mixture derived from the second mixture to form a first product comprising ≥1.0 wt. % of $C_{3+}$ aldehyde and/or $C_{3+}$ alcohol based on the weight of the product, the third mixture comprising molecular hydrogen, carbon monoxide, ≥1.0 wt. % of $C_2$ unsaturates (and optionally ≥1.0 wt. % of acetylene) based on the weight of the third mixture, wherein the third mixture has (i) a CO:$C_2$ unsaturates molar ratio in the range of 0.1 to 2.0, such as in the range of 0.15 to 1.2, and (ii) a molecular hydrogen:$C_2$ unsaturates molar ratio≥2.0. Optionally the third mixture has a carbon dioxide:$C_2$ unsaturates molar ratio≤0.30. Optionally, the process further comprises exothermically reacting at least a portion of the first and second reactants of a fourth mixture in a second region of the reverse-flow, regenerative pyrolysis reactor to produce a fifth mixture. The exothermic reacting of the fourth mixture's first and second reactants provides at least a portion of the heat utilized in the first region for deriving the second mixture from the first mixture. The first and second regions can be at least partially coextensive, for example, and the exothermic reacting of the fourth mixture's reactants can be conducted at a substantially different time than the pyrolysis.

Selected embodiments for producing one or more of $C_{3+}$ aldehyde, $C_{3+}$ alcohol, or ethylene from (i) the second mixture and/or (ii) a third mixture derived from the second mixture will now be described in more detail with reference to FIGS. 2a-2c. This description is not meant to foreclose other embodiments within the broader scope of the invention.

In one embodiment shown in FIG. 2a, stage 206 comprises a reverse-flow, regenerative pyrolysis reactor. In accordance with this embodiment, the first mixture is conducted to a first region 2064 of the reverse-flow, regenerative pyrolysis reactor via at least one conduit 2046. The first and second reactants of the fourth mixture are conducted to a second region 2063 of the reactor via conduit 305. The first and second reactants are conducted to region 2063 through separate channels within conduit 305, the first and second reactants being combined to produce the fourth mixture (for the exothermic reaction) in proximity to the downstream end of conduit 305 and the upstream end of region 2063. In another embodiment, the first reactant is conducted to region 2063 via conduit 305, with the second reactant being conducted to region 2063 via a second conduit 3051 (not shown).

In the illustrative embodiment, the first and second regions are at least partially coextensive as shown. The first mixture is derived from one or more source materials 200, e.g., natural gas, air, etc. Optionally, one or more of the source materials are upgraded in optional preparation stage 204 to produce the first mixture. The fourth mixture comprises first and second reactants. The first reactant can be, e.g., fuel, and the second reactant can be e.g., oxidant. The fuel can be derived from at least one second source material 300, e.g., natural gas, petroleum, other hydrocarbon, etc., including fractions, products, or byproducts thereof. The oxidant can comprise, e.g., oxygen, etc. and can be derived, e.g., from a source material (not shown) such as air. Optionally, one or more of the fourth mixture's source materials is upgraded in a second preparation stage 302 upstream of conduit 305 and optional conduit 3051 (not shown). Stage 302 can optionally include one or more of separation, conversion, addition of recycled portions of the second and/or fifth mixtures, etc. In this embodiment, the reactor of stage 206 is (i) "reverse flow" in the sense that upstream region of the reactor with respect to the first mixture is the downstream region with respect to the fourth mixture and (ii) "regenerative" in the sense that at least a portion of the heat consumed during the conversion of the first mixture is provided by oxidizing the fourth mixture.

Continuing with the illustrative embodiment of FIG. 2a, fuel is conducted via a first channel (or plurality thereof) in conduit 305 and oxidant is conducted via a second channel (or plurality thereof) in conduit 305 or optionally via a second conduit 3051 (not shown) to the second region 2063. Although the invention is described in terms of a fourth mixture comprising fuel and oxidant, the invention is not limited thereto, and this description is not meant to foreclose other first and second reactants within the broader scope of the invention. Optionally, at least a portion of conduit 305 (and/or conduit 3051 when utilized) is located within the reactor of stage 206.

Proximate to the downstream end of conduit 305 (or 305 and 3051), the fuel and oxidant are combined to produce the fourth mixture, the fuel and oxidant then reacting exothermically in the second region 2063 (the flow of the first and second reactants and the products thereof being represented by dashed line 2062). The exothermic reaction provides at least a portion of the heat utilized in the coextensive portion of region 2064 during the pyrolysis. The fifth mixture, comprising at least a portion of the compositions resulting from the reaction of the fourth mixture's fuel and oxidant (and optionally including a portion of the fourth mixture that is not consumed in the reaction), is conducted away from stage 206 via a conduit 2066. Optionally, at least a portion of conduit 2066 is located within the reactor of stage 206.

After at least a portion of the fourth mixture's fuel and oxidant are exothermically reacted in region 2063 (e.g., by an oxidation reaction such as combustion), the first mixture is conducted to the upstream end of region 2064 via conduit 2046. Optionally, at least a portion of conduit 2046 is located within the reactor of stage 206. The first mixture traverses region 2064 (the traversal being represented by solid line 2061), abstracting heat from region 2064 and thereby deriving the second mixture. In this embodiment, at least a portion of the heat abstracted by the first mixture in region 2064 is produced in region 2063 by the reaction of the first and second reactants. Optionally, a major amount of the heat abstraction occurs in the portion of region 2064 that is coextensive with region 2063. The second mixture is conducted away from stage 206 via at least one conduit 2065. Optionally, at least a portion of conduit 2065 is located within the reactor of stage 206. In an embodiment, conduit 2065 comprises at least a portion of the channels within conduit 305, which can serve, e.g., to preheat the fuel and/or oxidant of the fourth mixture before combustion.

Optionally, after at least a portion of the second mixture is conducted away from region 2064, the fuel and oxidant utilized to produce the fourth mixture are again conducted through separate channels within conduit 305 to region 2063, and the process repeats in sequence—exothermically reacting the fuel and oxidant of the fourth mixture to heat the reactor and then utilizing at least a portion of the heat for pyrolysing the first mixture. The process can thus be operated sequentially, e.g., continuously, semi-continuously, or even in batch mode. In an embodiment, stage 206 comprises a plurality of pyrolysis reactors operating, e.g., in series, parallel, or a combination thereof.

Continuing with the illustrative embodiment of FIG. 2a, a third mixture derived from at least a portion of the second mixture is conducted via conduit 2081 to a conversion stage 210, for converting at least a portion of the third mixture's $C_2$ unsaturates to a first product comprising $C_{3+}$ aldehyde and $C_{3+}$ alcohol. The embodiment of FIG. 2a can include optional components, as shown. For example, the first product can be conducted away from conversion stage 210 via conduit 2101 to an optional separation stage 211. Stage 211 can be utilized for one or more of (i) separating from the first product a mixture comprising $C_{3+}$ aldehyde and/or $C_{3+}$ alcohol; (ii) separating a mixture comprising one or more of molecular hydrogen, carbon monoxide, saturated hydrocarbon (such as methane), or $C_2$ unsaturates; or (iii) separating a mixture comprising one or more of molecular hydrogen, carbon monoxide, or saturated hydrocarbon. Conventional separations can be utilized in stage 211, but the invention is not limited thereto. Mixture (i) can be conducted away from stage 211 via conduit 2113, e.g., for converting, in optional second conversion stage 212, at least a portion of the aldehyde and alcohol of mixture (i) to a second product comprising olefin, e.g., propylene, which can be conducted away via a conduit 2121. The olefin can be polymerized if desired. Mixture (ii) can be conducted away from stage 211 via conduit 2111. Mixture (iii) can be conducted away via conduit 2112, e.g., for increasing the amount of molecular hydrogen, saturated hydrocarbon, and/or carbon monoxide in one or more of the first, third, fourth, or fifth mixtures.

The process can also include optional first upgrading stage 208 for deriving the third mixture from the second mixture, e.g., by separating one or more of molecular hydrogen (conduit 2082), light saturated hydrocarbon such as methane (conduit 2083), non-volatiles (conduit 2084), or heteroatom species such as hydrogen sulfide (conduit 2085). A sixth mixture comprising $C_2$ unsaturates can be derived from the second mixture by e.g., (i) dividing the sixth mixture from the second mixture (e.g., utilizing a splitter) and/or (ii) by separations means such as contacting the second mixture with a polar fluid such as one or more of furfural, phenol, n-methyl-2-pyrrolidone, etc. to remove at least a portion of the second mixture's acetylene, and then separating at least a portion of the removed acetylene from the polar fluid to produce the sixth mixture. The polar liquid can be added to stage 208 via conduit 2086, and can be regenerated and re-used if desired, as shown in FIG. 2b. When a splitter is utilized to produce the sixth mixture, stage 208 can include means for adjusting the third mixture's acetylene:ethylene molar ratio. Such means can include, e.g., a catalytic acetylene conversion, such as those utilizing one or more acetylene conversion catalysts. Optionally, the sixth mixture comprises ≥1.0 wt. % acetylene based on the weight of the sixth mixture and further comprises one or more of ethylene, carbon monoxide, molecular hydrogen, and light saturated hydrocarbon such as methane. The process can also include conducting the sixth mixture away from stage 208 via conduit 2087 to optional converter stage 215 for converting at least a portion of the sixth mixture's acetylene to produce a seventh mixture comprising (i) ≥1.0 wt. % of one or more of ethylene, benzene, toluene, or xylene based on the weight of the seventh mixture and optionally (ii) one or more of molecular hydrogen, saturated hydrocarbon such as methane, or carbon monoxide. When it is desired to operate the stage 215 with additional acetylene, ethylene, hydrogen, methane, or carbon monoxide, one or more of these can be obtained from mixture (ii) and conducted to stage 215 via conduit 2111, as shown in FIG. 2b. The process can further include conducting the seventh mixture via conduit 2152 to optional separation stage 216, for separating from the seventh mixture (i) a third product comprising ethylene (conducted away via conduit 2161) and (ii) a mixture comprising one or more of molecular hydrogen, saturated hydrocarbon, or carbon monoxide (conducted away via conduit 2162). When liquid-phase acetylene conversion is utilized in stage 215, the sixth mixture can further comprise at least a portion of the polar fluid utilized for acetylene separation in stage 208. In this case, stage 216 can further include separating at least a portion of any polar fluid in the seventh mixture, e.g., for recycle to stage 208. Conventional acetylene conversion technology can be used, but the invention is not limited thereto. For example, the acetylene converter can utilize acetylene conversion catalysts having an increased selectivity for ethylene in the presence of carbon monoxide. When the sixth mixture contains more carbon monoxide than is needed for increasing the conversion catalyst's ethylene selectivity, the excess carbon monoxide can be separated from the sixth mixture and utilized, e.g., for increasing the amount of carbon monoxide in the third mixture. The third product's ethylene can be polymerized if desired, e.g., the ethylene can be copolymerized with the olefin of the second product.

The process can also include a second upgrading stage 308 for upgrading the fifth mixture downstream of conduit 2066. One or more conduits can be utilized for conducting away a first byproduct from upgrading stage 308, the first byproduct comprising one or more of non-oxidized hydrocarbon (via conduit 3081), oxygenate (via conduit 3082); or heteroatom species such as $NO_x$, $SO_x$, $N_2$, sulfuric acid, etc. (via conduit 3083). When there is a need for additional carbon monoxide and/or molecular hydrogen, these can be produced in stage 214 (e.g., in a syngas generation unit), the carbon monoxide being conducted away via conduit 2141 and the molecular hydrogen being conducted away via a conduit 2142. Carbon monoxide and/or molecular hydrogen obtained from stage 214 can be conducted to stage 208 via conduits 2088 and 2089, e.g., for increasing the relative amounts of these species in the third and/or sixth mixtures. Stage 302 can be utilized for adjusting the compositions and relative amounts of the fourth mixture's fuel and/or oxidants as shown in FIG. 2a. For example, conduits can utilized for adding to the fourth mixture's fuel source materials one or more of light saturated hydrocarbon such as methane 3001 or diluent 3002; and conduits can be utilized for adding to the fourth mixture's oxidant source materials additional or supplemental oxidant 3003. Similarly, stage 204 can be utilized for adding to the first source material one or more of diluent (conduit 2043), hydrocarbon, e.g., light saturated hydrocarbon such as methane (conduit 2044), or oxygenate (conduit 2045); molecular hydrogen (conduit 2042), and/or for conducting away heteroatom species such as hydrogen sulfide or non-volatiles (conduit 2041). In another embodiment, shown in FIG. 2C, at least a portion of the second mixture is conducted from stage 206 to stage 210 via conduit 2065. The effluent of stage 210 is conducted to optional separation stage 211. A first stream comprising $C_{3+}$ aldehyde and/or $C_{3+}$ alcohol is conducted away from stage 211 via conduit 2113. A second stream comprising one or more of saturated hydrocarbon, molecular hydrogen, or carbon monoxide is conducted away from stage 211 via conduit 2112. A third stream comprising acetylene, and optionally one or more of ethylene, carbon monoxide, molecular hydrogen, or saturated hydrocarbon is conducted away from stage 211 via conduit 2111, at least a portion of the third stream's acetylene is converted to ethylene in optional conversion stage 217.

In one or more embodiments, (a) the first, second, and third mixtures are substantially the same as those described in sections I and III and (b) stages 204, 206, 208, 210, and 212 operate substantially the same way as described in sections I and IV. Although the invention is not limited thereto, conventional separations technology can be utilized in stages 211 and 216, and conventional acetylene conversion technology can be utilized in stages 215 and 217. The fourth and fifth mixtures will now be described in more detail.

VII. Fourth and Fifth Mixtures

Exothermically reacting first and second reactants can provide at least a portion of the heat utilized by the pyrolysis. For example, the first and second reactants can be mixed within a pyrolysis reactor to produce a fourth mixture, the first and second reactants then reacting, e.g., by an oxidation reaction such as combustion, as the fourth mixture traverses at least a portion of the pyrolysis reactor. In another embodiment, the first and second reactants are combined upstream of the pyrolysis reactor, with at least a portion of the first and second reactants exothermically reacting within the pyrolysis reactor. The first reactant can comprise, e.g., fuel such as molecular hydrogen, synthesis gas (mixtures of CO and $H_2$), or hydrocarbon, such as ≥10.0 wt. % hydrocarbon (including mixtures thereof), or ≥50.0 wt. % hydrocarbon, or ≥90.0 wt. % hydrocarbon based on the weight of the first reactant. The second reactant can comprise, e.g., ≥10.0 oxidant, e.g., or ≥50.0 wt. % oxidant, or ≥90.0 wt. % oxidant based on the weight of the second reactant. Optionally, the fourth mixture further comprises diluent. When the first reactant comprises hydrocarbon, the particular hydrocarbon selected is not critical. For example, in an embodiment, the hydrocarbon comprises one or more of the hydrocarbons specified for the first mixture, e.g., methane. In an embodiment, the hydrocarbon is derived from, comprises, consists essentially of, or consists of one or more of gases derived from Fischer-Tropsch processes, methane, methane containing streams such as coal bed methane, biogas, associated gas, natural gas and mixtures or components thereof, etc. When the first reactant comprises hydrogen and/or hydrocarbon and the second reactant comprises oxidant, the choice of oxidant is not critical, provided the oxidant is capable of exothermically reacting with the hydrogen and/or hydrocarbon. For example, in an embodiment, the oxidant comprises, e.g., molecular oxygen.

Referring to FIGS. 2a-2c, in cases where the fuel source material(s) 300 are too lean in one or more of hydrocarbon (e.g., light hydrocarbon such as methane) or diluent, these can be added through one or more of conduits 3001 or 3002. When the source materials do not contain sufficient oxidant, it can be added to stage 302 via one or more conduits 3003. For example, in some embodiments it is beneficial to increase the amount of oxidant in the fourth mixture beyond that needed to oxidize substantially all of the fourth mixture's fuel, e.g., in embodiments where the pyrolysis of the first mixture deposits a hydrocarbon-containing residue in the pyrolysis reactor and the process would benefit from oxidizing at least a portion of the residue. In other embodiments, it is beneficial to lessen the amount of oxidant in the fourth mixture, e.g., when it is desired to conduct the oxidizing of the fourth mixture under partial oxidation conditions. In still other embodiments, it is beneficial for the fourth mixture to contain a substantially stoichiometric amount of oxidant, i.e., the amount of oxidant needed to oxidize substantially all of the fourth mixture's fuel.

Optionally, the fourth mixture further comprises diluent, e.g., ≥1.0 wt. % of diluent based on the weight of the first mixture. Suitable diluents (which can be a diluent mixture) include one or more of, e.g., water, carbon dioxide, non-combustible species, nitrogen ($N_2$), hydrogen sulfide, $C_{4+}$ mercaptans, amines, mixtures of amines, non-hydrocarbon non-volatiles (whether combustible or not) including refractory inorganics such as refractory oxygenates, inert gas (including inert gas mixtures), etc. In an embodiment, the fourth mixture comprises ≤96.0 wt. % diluent, e.g., in the range of 65.0 wt. % to 94.5 wt. % diluent, based on the weight of the fourth mixture.

In an embodiment, the fourth mixture comprises ≥1.0 wt. % molecular oxygen, e.g., in the range of 5.0 wt. % to 25.0 wt. %, such as 7.0 wt. % to 15.0 wt. %; ≥0.1 wt. % fuel, e.g., in the range of 0.5 wt. % to 10.0 wt. %, such as 1.0 wt. % to 5.0 wt. %, the weight percents being based on the weight of the fourth mixture, with the balance of the fourth mixture being diluent.

The fifth mixture comprises (i) products derived from the exothermic reaction of the fourth mixture's first and second reactants, (ii) diluent, when diluent is present in the fourth mixture, and optionally (iii) unreacted first and/or second reactants and/or (iv) products derived from the oxidation of components of the second mixture remaining in stage 206 after the pyrolysis. e.g., products derived from the oxidation combustible non-volatiles such as coke. When the exothermic reaction of the first and second reactants involves hydrocarbon combustion, or when a diluent is present in the fourth mixture (such as $N_2$ or $H_2S$), the fifth mixture can comprise carbon dioxide, and can further comprise sulfur oxides, nitrogen oxides, etc.

A continuous or semi-continuous process for deriving (a) the second mixture from the first mixture and (b) the fifth mixture from the fourth mixture will now be described in more detail. Although the process is described in terms of a reverse-flow, regenerative pyrolysis reactor, the invention is not limited thereto, and this description is not meant to foreclose other embodiments within the broader scope of the invention.

VIII. Continuous or Semi-Continuous Process

Referring to FIGS. 2a-2c, the first reactant is conducted via one or more first channels within conduit 305 and the second reactant is conducted via one or more second channels within conduit 305 or optionally via a second conduit 3051 (not shown). The first and second reactants are thus conducted separately to the upstream end of region 2063, where the first and second reactants are combined to form the fourth mixture. A fifth mixture, derived from the exothermic reacting of at least a portion of the fourth mixture's first and second reactants in region 2063, is conducted away from stage 206 via conduit 2066. In an embodiment, the first reactant is fuel and the second reactant is oxidant, the reacting including a combustion or partial combustion of at least a portion of the fuel utilizing at least a portion of the oxidant. At least a portion of the heat of combustion is utilized to increase the temperature of region 2064. At the conclusion of the combustion step, the fifth mixture is conducted away via conduit 2066 and the first mixture is introduced into the reactor (optionally after an optional purge of the fifth mixture from stage 206 by a non-reacting material such as an inert purge gas). The relative types and amounts of the first and second reactants are selected so that the (exothermic) heat of reaction obtained during the reaction sufficiently heats region 2064, particularly the portion of region 2064 that is coextensive with region 2063, for at least partially pyrolysing the first mixture.

Pyrolysis reactor of stage 206 can be, e.g., one or more of the pyrolysis reactors described in U.S. Patent App. Pub. No. 2007/0191664. For example, the reactors of that reference provide a high-temperature heat bubble formed in the middle of a packed-bed reactor system. The reactor system can be utilized in a two-step process wherein heat is (1) added to the bed via in-situ combustion (e.g., of the fourth mixture) and then (2) removed from the bed via pyrolysis (e.g., in-situ endothermic reforming of the first mixture). For example, in one embodiment the reactor system comprises two reactors: (a) a first (heat recuperating) reactor and (b) a second (pyrolysis) reactor. Deriving the second mixture from the first mixture in such a system does not require a catalyst, though one can be used, e.g., to optionally convert light hydrocarbon (e.g., methane) in the first mixture to acetylene.

The reactor system can operate, e.g., in series, parallel, or a combination thereof, and utilizes accompanying valve means for conducting the first, second, fourth and fifth mixtures to/from the reactors of the reactor system. For example, in one embodiment reactor system includes first and second reactors, oriented in a series relationship with each other with respect to a common flow path, optionally along a common axis. The common axis may be horizontal, vertical, or some other orientation with respect to the surface of the earth.

Segments of conduits 305 and 3051 can be in the form of separate but substantially parallel channels located within a quenching reactor bed (e.g., the first reactor), the first reactor being located within stage 206. In other words, in this embodiment the first and second reactants are conducted toward the second reactor via substantially independent flow paths (e.g., the first reactor can be a ceramic article with channels located therein). Optionally, the first and/or second reactants abstract heat from the first reactor. Optionally, other components utilized to produce the fourth mixture, e.g., diluent, can be conducted through the first reactor together with the first reactant, the second reactant, or a portion with each. When the components utilized to produce the fourth mixture (optionally heated by the hot first reactor) reach a designated location within the reactor system, the components are combined and at least a portion of the fourth mixture's first reactant exothermically reacts with at least a portion of the fourth mixture's second reactant in region 2063.

The exothermic reaction can include an oxidization (e.g., combustion) of the first reactant, the first reactant being, e.g., hydrogen and/or hydrocarbon. Such a combustion can result in a high temperature zone (also referred to by those skilled in the art as a temperature bubble), at least a portion of the temperature bubble being located in region 2063 and having a temperature $\geq 1.50 \times 10^{3}$° C., e.g., in the range of about $1.60 \times 10^{3}$° C. to about $1.70 \times 10^{3}$° C. Optionally, the combustion completely oxidizes the oxidizable species (e.g., fuel) in the first reactant, including hydrocarbon, hydrogen, etc. therein. The combustion also results in oxidizing at least a portion of any combustible non-volatiles remaining in stage 206 after the pyrolysis. Optionally, diluent such as nitrogen that may be present in the fourth mixture is not oxidized to a significant extent. Optionally, $\geq 50.0\%$ of the combustion (based on the amount of the fourth mixture, mole basis, that is oxidized in region 2063), e.g., $\geq 75.0\%$, such as $\geq 90.0\%$ of the combustion occurs in the portion of region 2063 that is located between the first and second reactors. Optionally, the combustion duration is for a time sufficient for (i) the removal of any combustible, non-volatiles from stage 206 and (ii) the second reactor to abstract heat from the combustion, the second reactor being located at least partially within zone 2063 but downstream of the first reactor with respect to the flow of the fourth mixture. In other words, the combustion optionally displaces the temperature bubble into and at least partially through the second reactor. For efficiency, it is generally undesirable to displace the temperature bubble past the downstream end (with respect to the flow of the fourth and fifth mixtures) of the second reactor, e.g., to avoid waste of heat and/or overheating the second reactor. In an embodiment, the fifth mixture, derived from the combustion of the fourth mixture, is conducted through the second reactor and away from stage 206.

Optionally, the total amount of heat added to the reactor system during the exothermic reaction of the first and second reactants (e.g., the regeneration step) does not exceed the sum of the heats that are required (a) to sustain the pyrolysis reaction for endothermically driving the second mixture from the pyrolysis portion of the first mixture and (b) for heat losses from the system, e.g., by as conduction losses through reactor walls and/or convective losses with, e.g., the second mixture. Optionally, the total amount of heat stored in the reactor system though is generally much more than the minimum amount of heat needed for the pyrolysis in any single cycle of a continuous or semi-continuous process.

After at least a portion of the fourth mixture's hydrocarbon has been oxidized, the pyrolysis portion of the first mixture is conducted to the upstream end of region 2064, e.g., the upstream end of the second reactor, where upstream is now defined with respect to the flow of the first and second mixtures. Optionally, a reactor purge can be used between the oxidation and pyrolysis steps. Optionally, the first mixture is exposed to a temperature $\geq 1.50 \times 10^{3}$° C. under high severity thermal pyrolysis conditions, e.g., in the portion of region 2064 that is coextensive with region 2063 via proximity to the second reactor and other reactor internals (e.g., mixer media) located, e.g., in the temperature bubble region, which have been heated by the exothermic reaction of the first and second reactants. Optionally, at least a portion of the temperature bubble region is located within the portion of zone 2064 that is coextensive with zone 2063. Optionally, an inert gas sweep is used before the combustion and/or pyrolysis steps of the process.

Figure 3A:
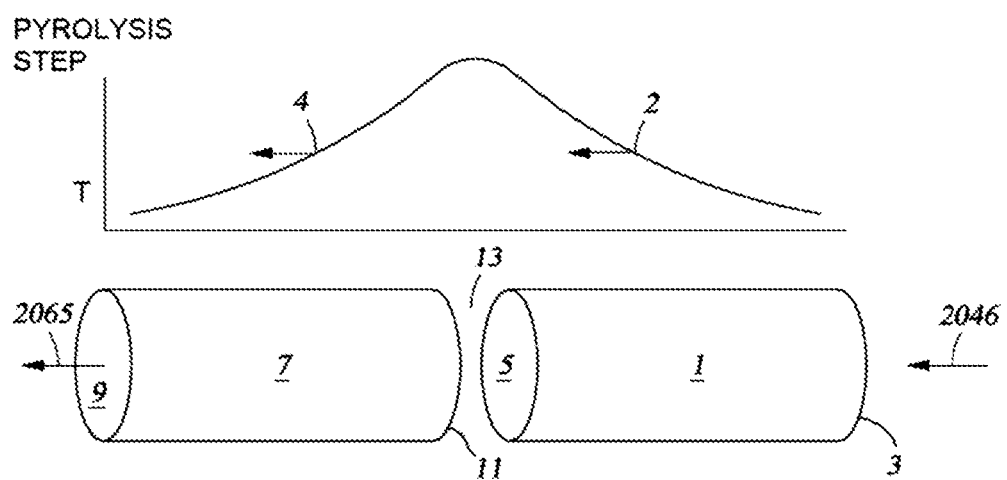
FIGS. 3a and 3b schematically show the flow of the first, second, fourth, and fifth mixtures in a regenerative, reverse-flow, pyrolysis reactor.
Figure 3B:
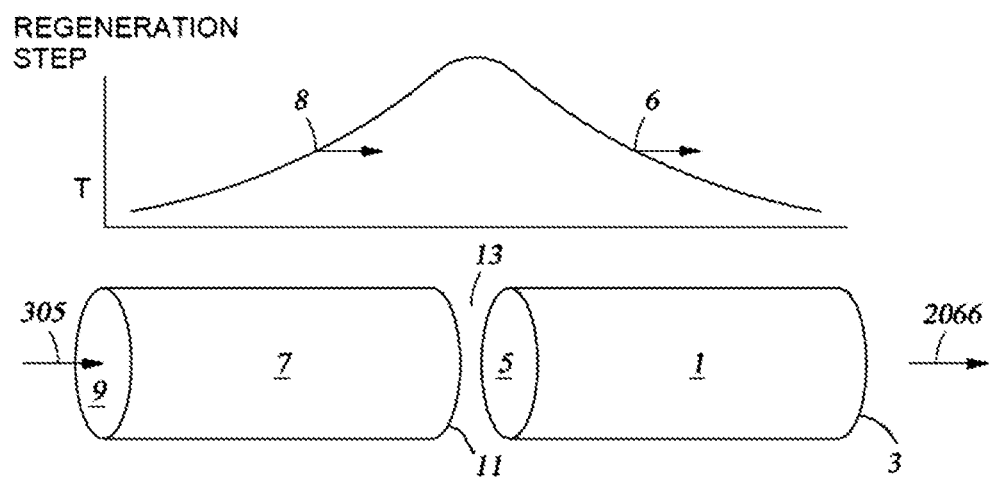

Stage 206 can include a reactor system shown schematically in FIGS. 3a and 3b. The reactor system comprises two reactors: a first (recuperator/quenching) reactor 7 and a second (pyrolysis) reactor 1. Optionally, the first and second reactors both contain regenerative beds, where the term "regenerative bed" means a reactor bed comprising materials that are effective in storing and transferring heat, and optionally useful for carrying out a chemical reaction. In an embodiment, the regenerative beds comprise bedding or packing material, such as glass or ceramic beads or spheres, metal beads or spheres, ceramic (including. e.g., alumina, yttria, zirconia, etc., and mixtures thereof) or metal honeycomb materials, ceramic tubes, extruded monoliths, catalysts, etc. Optionally, the materials comprising the regenerative bed maintain integrity, functionality, and withstand long term exposure to temperatures in excess of 1200° C., preferably in excess of 1500° C., more preferably in excess of 1700° C., and even more preferably in excess of 2000° C. for operating margin.

Figure 2D:
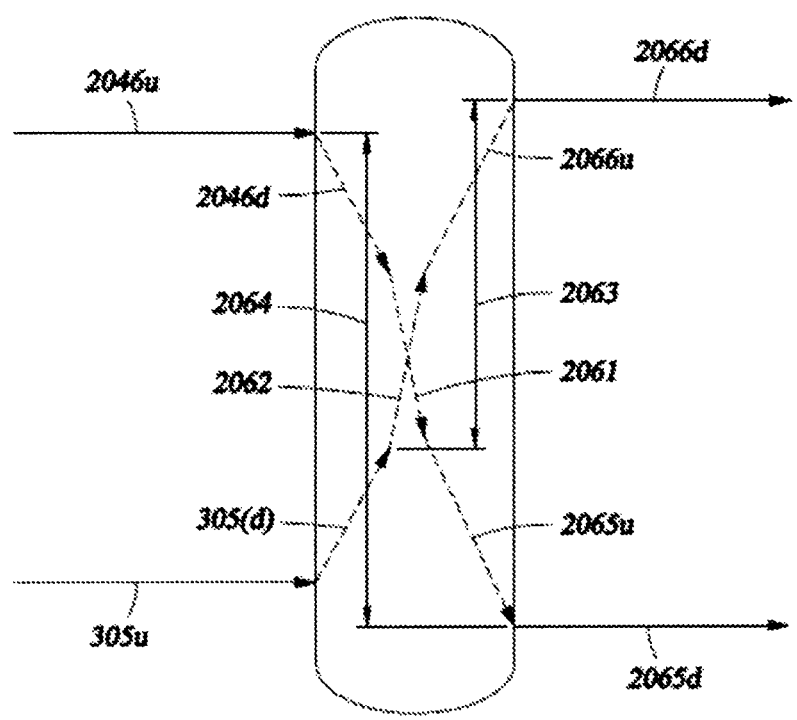
FIG. 2d schematically shows the flow of the first, second, fourth, and fifth mixtures within a reverse-flow pyrolysis reactor.

The continuous or semi-continuous process can begin with "pyrolysis" step wherein (a) the downstream end 5 of the second reactor 1 (downstream with respect to the flow of the first mixture, as shown in FIG. 3a) is at a temperature greater than that of the upstream end 3 and (b) at least a portion (including the downstream end 9) of the first reactor 7 is at a temperature less than that of the downstream end of the second reactor 5 in order to provide a quenching effect for the second mixture. The first mixture is conducted to the upstream end 3 of the second reactor via conduit 2046. Optionally, conduit 2046 comprises upstream 2046u and downstream segments 2046d, as shown in FIG. 2d. Upstream segment 2046u (represented in the Fig. by a solid line) is external to the second reactor 1. Downstream segment 2046d (represented by a dashed line), is in fluid communication with 2046u and is located within second reactor 1, e.g., as one or more channels within the reactor.

Continuing with reference to FIG. 3a, the first mixture abstracts heat from the first reactor, resulting in the derivation of the second mixture from the first by pyrolysis. As this step proceeds, a shift in the temperature profile 2 occurs (e.g., a shift in the trailing edge of the temperature bubble as indicated by the arrow), the amount of this shift being influenced by, e.g., the heat capacity and/or heat transfer properties of the system. At least a portion of the second mixture, e.g., the portion in the vapor phase, is conducted from the downstream end 5 of the second reactor to the upstream end 11 of the first reactor 7, and is conducted away from the first reactor via conduit 2065 proximate to the downstream end 9, as shown. Optionally, conduit 2065 comprises upstream 2065u and downstream segments 2065d, as shown in FIG. 2d. Downstream segment 2065d (represented in the Fig. by a solid line) is external to the first reactor 7. Upstream segment 2065u (represented by a dashed line), is in fluid communication with 2065d and is located within the first reactor 7. e.g., as one or more channels within the reactor. At the start of pyrolysis, the first reactor 7 has a temperature less than that of the second reactor 1. As the second mixture traverses the first reactor 7, the second mixture is quenched (e.g., cooled) to a temperature approaching that of the downstream end 9 of the first reactor. As the second mixture is quenched in the first reactor 7, the leading edge of the temperature bubble 4 moves toward the downstream end 9 of the first reactor 7. In at least one of the embodiments represented by FIG. 3a, the upstream end of pyrolysis region 2064 (referenced in FIGS. 2a-2c) is proximate to the upstream end 3 of the second reactor 1. The downstream end of pyrolysis region 2064 is proximate to the downstream end 9 of the first reactor 7. Since the quenching heats the first reactor 7, the combustion step can include cooling the first reactor, e.g., to shift the leading edge of the temperature bubble away from end 9 of the first reactor 7, as illustrated schematically in FIG. 3b.

The pyrolysis step can include one or more of the following conditions: the first mixture achieves a peak pyrolysis gas temperature $\geq 1.20\times 10^3$° C., e.g., in the range of $1.40\times 10^3$° C. to $2.20\times 10^3$° C., such as, $1.50\times 10^3$° C. to $1.90\times 10^3$° C., or $1.60\times 10^3$° C. to $1.70\times 10^3$° C.; a total pressure $\geq 1.0$ bar (absolute), e.g., in the range of 1.0 bar to about 15.0 bar, such as in the range of 2.0 bar to 10.0 bar; and/or a high-severity residence time$\leq 0.1$ seconds. e.g., $\leq 5.0\times 10^{-2}$ seconds. When it is desired to increase the amount of one or more of hydrogen, light saturated hydrocarbon, and oxygenate in the first mixture, these can be added (e.g., in stage 204) as follows:

(i) Molecular hydrogen can be added via conduit 2042, with the added hydrogen obtained, e.g., from one or more of (a) from the process via conduit 2082 when optional stage 208 is present, (b) from molecular hydrogen separated from the first, second, or third product, or (c) from an external source, e.g., an optional synthesis gas generation process 214 via conduit 2142;

(ii) Hydrocarbon (e.g., light saturated hydrocarbon) can be added via conduit 2044. These species can be obtained from the process via conduit 3081 or 2083. e.g., when optional stages 308 and 208 are utilized;

(iii) Oxygenate can be added via conduit 2045. The oxygenate can be obtained, e.g., (a) from the process via conduit 3082, when optional stage 308 is utilized, (b) from carbon monoxide separated from the first product, (c) steam, e.g., steam generated in a process cooler, (d) carbon dioxide separated from the second mixture in stage 208, or (e) from a source external to the process, e.g., conduit 2141 when optional syngas generation process 214 is utilized; and (iv) Diluent can be added via conduit 2043.

In an embodiment, a purge gas can be utilized to remove pyrolysis products from stage 206 after the pyrolysis step and before the combustion step begins. It is understood that flow control means (e.g., one or more of valves, rotating reactor beds, check valves, louvers, flow restrictors, timing systems, etc.) can be used to control gas flow, actuation, timing, and to alternate physical beds between the flow systems for the first, second, fourth, and fifth mixtures, and the optionally purge gas, if any. The combustion step will now be described in more detail, with reference to FIG. 3b.

The second step of the process, referred to as the combustion or regeneration step, begins by separately conducting first and second reactants to the first reactor 7, with the term "upstream" now being with respect to the flow of the fourth mixture, as shown in FIG. 3b. The first and second reactants are conducted to first reactor 7 via conduit (or a plurality of conduits) 305 and optionally 3051 (not shown). The first reactant can be conducted via a first channel (or plurality thereof) located within conduit 305, and the second reactant is separately (and optionally simultaneously) conducted via a second channel (or plurality thereof) within conduit 305 or via a channel or plurality thereof in a second conduit 3051 (not shown). Optionally, conduit 305 comprises upstream 305u and downstream segments 305d, as shown in FIG. 2d. Upstream segment 305u (represented in the figure by a solid line) is external to first reactor 7. Downstream segment 305d (represented by a dashed line), is in fluid communication with 305u and is located within first reactor 7, e.g., as one or more channels therein. When conduit 3051 is utilized to convey the second reactant, conduit 3051 can comprise upstream 3051u and downstream 3051d segments; 3051u and 3051d being in fluid communication, and wherein (a) 3051u is located external to first reactor 7 and (b) 3051d is located within first reactor 7, e.g., as one or more of a second set of channels therein, the first set of channels being those of conduit 305d. Conduits 305 and 3051 can include one or more spargers and/or distributors for conveying the first and second reactants from upstream segments 305u and 3051u into downstream segments 305*d* and 3051*d*. Suitable spargers, distributors, and configurations for using these to connect conduit segments are disclosed in U.S. Pat. No. 7,815,873, which is incorporated by reference herein in its entirety. Accordingly, the first and second reactants separately traverse first reactor 7 through their separate channels (in other words, the first and second reactants do not mix appreciably in the first reactor) and exit the downstream end 11 of the first reactor 7 where the first and second reactants are combined to produce a fourth mixture. The first and second reactants react exothermically at or proximate to a central region 13 of the reactor system. Optionally, the exothermic reaction continues downstream (with respect to the average flow of the fourth mixture) of region 13, e.g., in second reactor 1. Although this embodiment is described in terms of the first and second reactants separately traversing first reactor 7, the invention is not limited thereto, and this description is not meant to foreclose other embodiments within the broader scope of the invention, such as (a) embodiments where the first and second reactants are mixed to produce the fourth mixture, with the fourth mixture traversing reactor 7; or (b) embodiments where the first reactant is conducted into and through first reactor 7 via conduit 305 with the second reactant being conducted to region 13 via conduit 3051 by a path external to first reactor 7. The fifth mixture, comprising any unreacted fourth mixture, products resulting from the reaction of the first and second reactants and at least a portion of any combustible, non-volatiles retained in stage 206 after the pyrolysis, is conducted away from second reactor 1 via one or more conduits 2066. Optionally, conduit 2066 comprises upstream 2066*u* and downstream segments 2066*d*, as shown in FIG. 2*d*. Downstream segment 2066*d* (represented in the figure by a solid line) is external to second reactor 1. Upstream segment 2066*u* (represented by a dashed line), is in fluid communication with 2066*d* and is located within the second reactor 1, e.g., as one or more channels within the reactor.

The combustion step thus includes the following features: (i) heating of region 13 and the second reactor 1 by transferring at least a portion of the heat of combustion to the reactor system downstream of the end 11 of the first reactor and (ii) by transferring at least a portion of the sensible heat recovered by the first and second reactants in an upstream region of the first reactor (upstream with respect to the flow of the fourth mixture and components thereof) toward one or more of the downstream region of the first reactor, region 13, and the second reactor in order to thermally regenerate the reactor system. Accordingly, the trailing edge 8 and leading edge 6 of the temperature bubble translate downstream from their starting locations at the beginning of the combustion step, as shown in FIG. 3*b*.

In the embodiment of FIG. 3*b*, the exothermic reaction region 2063 can be located, e.g., between a first point proximate to the downstream end 11 of first reactor 7 and a second point proximate to the downstream end 3 of second reactor 1, "downstream" being with respect to the average flow of the fourth mixture. Referring to FIG. 3*b*, the pyrolysis region 2064 can be located, e.g., between a first point proximate to the upstream end 3 of the second reactor 1 and a second point proximate to the downstream end 9 of first reactor 7, "upstream" and "downstream" being with respect to the average flow of the first mixture. Referring now to FIG. 2*d*, it should be appreciated that the invention can be practiced without precisely defining (a) the boundaries of regions 2063 and 2064, (b) the precise locations of the intersections of flow-path 2062 with segments 305*d* and 2066*u*, or (c) the precise locations of the intersections of flow-path 2061 with segments 2046*d* and 2065*u* (the intersection locations being schematically depicted by inflections). Although region 2063 (the exothermic reaction region) is at least partially coextensive with pyrolysis region 2064, the upstream end of region 2063 ("upstream" with respect to the average flow of the fourth mixture) is proximate to the location where sufficient first and second reactants have combined to produce an exothermic reaction, this location being indicated in FIG. 2*d* as an inflection between segment 305*d* and flow-path 2062. The downstream end of region 2063 is generally proximate to the downstream end of second reactor 1 though this is not required, and in at least one embodiment the downstream end of region 2063 is located further downstream, e.g., in conduit 2066*d*. The intersection of flow-path 2062 (which encompasses at least a portion of region 13 and optionally, e.g., at least a portion of reactor 1) with segment 305*d* (and 3051*d*) is generally proximate to the downstream end 11 of first reactor 7 (downstream with respect to the average flow of the fourth mixture), since that is where the first and second reactants combine. The practice of the invention does not require precisely defining the intersection of flow-path 2062 and segment 2066*u*. The practice of the invention does not require precisely defining the intersection of flow path 2061 (which encompasses at least a portion of region 13 and optionally, e.g., portions of reactors 1 and/or 7 and segments 2046*d* and 2065*u*). It should be recognized that the oscillatory translation of the leading and trailing edges of the temperature bubble during the combustion and pyrolysis steps confines the temperature bubble (which can achieve temperatures e.g., >1600° C.) to regions of the reactor system that can tolerate such conditions long-term.

At least a portion of the means utilized for conveying the first mixture into and through the first reactor, e.g., at least a portion of conduit 2046*d*, can be also utilized for conveying at least a portion of the fifth mixture, e.g., as conduit 2066*u*. In an embodiment, at least a portion of the means utilized for conveying the first and second reactants, e.g., at least a portion of conduit 305*d* (and/or 3051*d*), is also utilized for conveying at least a portion of the second mixture, e.g., as conduit 2065*u*.

Optionally, (a) segment 305*d* comprises a plurality of first channels (each channel, e.g., comprising an independent flow path) in the first reactor 7 and (b) segment 3051*d* comprises a plurality of second channels that may have the same or different cross sectional shape and size compared to those of the plurality of first channels. In one embodiment, the first reactor includes the first and second plurality of channels interdigitated in a honeycomb monolith structure. Honeycomb monoliths include, e.g., extruded porous structures such as those that are used for automotive catalytic converters, etc. The term "honeycomb" means a cross-sectional shape that includes multiple flow paths or conduits through the extruded monolith, but the use of this term is not meant to limit the monolith's structure or shape to any particular topology. In embodiments where a honeycomb monolith is used, the honeycomb monolith enables low pressure loss transference while providing contact time and heat transfer. Optionally, a mixer is used between the first and second reactors to improve combustion. Mixer means, distributor means, reactor system internals, valve means, etc., for the reactor system included in stage 206 can be substantially the same as those described in U.S. Patent App. Pub. No. 2007/0191664, for example. Representative combustion conditions will now be described in more detail.

In an embodiment, the exothermic reaction of the first and second reactants of the fourth mixture includes combustion, the combustion conditions including a temperature $\geq 1.40 \times 10^{3}$° C., e.g., $\geq 1.50 \times 10^{3}$° C. such as $\geq 1.60 \times 10^{3}$° C., e.g., in the range of 1.90×10³° C. to 2.20×10³° C. and a pressure ≥1.0 bar (absolute), e.g., in the range of 1.0 bar to 15.0 bar, such as 2.0 bar to 5.0 bar. When it is desired to increase the relative amount of (i) one or more of hydrocarbon (e.g., methane) and/or hydrogen in the first reactant over that of its source material or (ii) increase the relative amount of oxidant (e.g., oxygen and/or ozone) in the second reactant over that of its source material, this can be done as follows:

(i) Hydrocarbon, such as light saturated hydrocarbon, e.g., methane, can be added via conduit 3001. These species can be obtained from (i) external sources and/or (ii) sources within the process such as from conduits 3081 or 2083, e.g., when optional stages 308 and 208 are utilized; and (ii) Oxidant can be added via conduit 3003. The added oxidant can be obtained from (i) external sources and/or (ii) sources within the process such as from conduit 3082 (when the oxygenate in conduit 3082 comprises oxidant). e.g., when optional stage 308 is utilized and/or from a source external to the process, e.g., line 2141 when optional syngas generation process 214 is utilized. When the source material is air, the air can be obtained from a blower or compressor, for example.

Continuing with reference to FIGS. 2a-2c, at the conclusion of the combustion step, optional upgrading stage 308 can be used, e.g., to separate from the fifth mixture species that may be useful in other stages of the process, e.g., via conduits 3081-3083 as discussed, e.g., a low-$O_2$ diluent can be separated from the fifth mixture and utilized to produce the fourth mixture. The portion of the second mixture that is not used in other stages of the process can be conducted away from the process via one or more conduits (not shown) for storage or further processing. At the conclusion of the pyrolysis step, optional upgrading stage 208 can be used, e.g., to separate from the second mixture species that may be useful in other stages of the process, e.g., via conduits 2082. Conventional separations processes are useful for stage 208 and 308, though the invention is not limited thereto. A third mixture having substantially the same composition as the vapor-phase portion of the second mixture (FIG. 2c) or derived therefrom (FIGS. 2a-2b) in optional stages 208 is then conducted to conversion stage 210. Conventional separations processes are useful for stages 208 and 308, though the invention is not limited thereto. In embodiments where downstream stages, e.g., hydroformylation stage 210 or acetylene conversion stage 215 operate at a higher pressure than the pyrolysis stage 206, means for increasing the second mixtures' pressure can be utilized, e.g., in stage 208 and locations downstream thereof. Conventional means for increasing pressure are suitable, e.g., one or more compressors, blowers, etc., though the invention is not limited thereto. Conventional acetylene hydrogenation can be utilized in stages 208, 215, and/or 217. Stages downstream of stage 206, including optional stages, can be operated in the continuous process as specified above in section VI.

Example

The following prophetic example is conducted. A first mixture is exposed to a time averaged (over the duration of the pyrolysis step) peak pyrolysis temperature of 1.625×10³° C. for a residence time of about 1.0×10² milliseconds at a total pressure of 5.0 bar (absolute) to produce a second mixture; the first mixture comprising 68.5 wt. % of methane, 17.1 wt. % of molecular hydrogen, and 14.4 wt. % of carbon monoxide (Effectiveness Factor of 1.0) based on the weight of the first mixture; and the second mixture comprising 18.1 wt. % of acetylene, 11.8 wt. % of ethylene, 20.5 wt. % of methane, 1.4 wt. % of ethane, 25.1 wt. % of molecular hydrogen, 8.6 wt. % of $C_{3+}$, and 14.4 wt. % of carbon monoxide based on the weight of the second mixture. For the purpose of this example, it is presumed that the $C_{3+}$ remains in the pyrolysis reactor as a deposit. Acetylene is separated from the second mixture by 30o contacting the second mixture with n-methyl-2-pyrrolidone, thereby producing a third mixture. The separated acetylene is recovered, and the n-methyl-2-pyrrolidone is recycled to the separator. The third mixture comprises 28.0 wt. % of methane, 19.6 wt. % of carbon monoxide, 34.2 wt. % of molecular hydrogen, 1.9 wt. % of ethane, and 16.2 wt. % of ethylene based on the weight of the third mixture. The third mixture is conducted to a hydroformylation stage wherein the third mixture contacts a hydroformylation catalyst at a temperature of 100.0° C. for a reaction time of 45 minutes. The hydroformylation catalyst and catalyst production method are the same as described in U.S. Pat. No. 5,675,041, Example 2. A product derived from the hydroformylation of the third mixture is conducted away from the hydroformylation stage, the product comprising 28.0 wt. % of methane, 3.5 wt. % of carbon monoxide, 31.9 wt. % of molecular hydrogen, 1.9 wt. % of ethane, and 34.6 wt. % of propanol based on the weight of the first product. A first stream comprising hydrogen, methane, and carbon monoxide is separated from the first product in stage 211 as shown in FIG. 2b. A portion of the first stream is conducted to stage 204, via conduit 2112, where it is utilized to produce the first mixture. A second stream comprising $C_2$ unsaturates, saturated hydrocarbon, molecular hydrogen, and carbon monoxide is also separated from the first product in stage 211. The second stream is conducted to stage 215 via conduit 2111, where the second stream is combined with the acetylene (in line 2087) recovered from the n-methyl-2-pyrrolidone to produce a mixture which contacts a conventional acetylene conversion catalyst comprising Pd at a temperature of 51.5° C. and a pressure of 13.4 bar (absolute) in stage 215 to produce a third product comprising ethylene. The third product is divided in stage 216 into first and second portions, the first portion being conducted away via line 2161 and the second portion being recycled to stage 215 via line 2162 and utilized in the acetylene conversion. The remainder of the first product following the separations in stage 211, the remainder comprising propanol, is conducted away via conduit 2113. A portion of the propanol is utilized to produce a second product comprising propylene in stage 212, the propylene being conducted away via conduit 2121.

The example demonstrates that the pyrolysis of the specified first mixture produces a second mixture comprising $C_2$ unsaturates and sufficient carbon monoxide to allow hydroformylation of at least a portion of the second mixture's $C_2$ unsaturates to $C_3$ alcohol, without producing carbon monoxide in too large an amount as would create gas-handling inefficiencies downstream of the pyrolysis.

All patents, test procedures, and other documents cited herein, including priority documents, are fully incorporated by reference to the extent such disclosure is not inconsistent and for all jurisdictions in which such incorporation is permitted.

While the illustrative forms disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which this disclosure pertains.

The invention claimed is:

1. A hydrocarbon conversion process, comprising:
   (a) providing a first mixture, the first mixture comprising hydrocarbon and oxygenate, wherein (i) the first mixture's hydrocarbon comprises hydrocarbon in natural gas and (ii) the first mixture's oxygenate comprises carbon dioxide in natural gas;
   (b) exposing the first mixture a temperature $\geq 1.40 \times 10^{3}$° C. in a first region under thermal pyrolysis conditions which include at a total pressure $\geq 0.1$ bar absolute to produce a second mixture, the second mixture comprising molecular hydrogen, carbon monoxide, and $\geq 1.0$ wt. % of $C_2$ unsaturates based on the weight of the second mixture, wherein the second mixture has a carbon monoxide:$C_2$ unsaturates molar ratio in the range of 0.1 to 2;
   (c) transferring to at least one converter (i) at least a portion of the second mixture and/or (ii) a third mixture derived from the second mixture, the transferred mixture comprising hydrogen, carbon monoxide, and $\geq 1.0$ wt. % of $C_2$ unsaturates based on the weight of the transferred mixture, wherein the transferred mixture has a CO:$C_2$ unsaturates molar ratio in the range of 0.1 to 2.0; and
   (d) converting $\geq 10.0$ wt. % of the transferred mixture's $C_2$ unsaturates, based on the weight of the transferred mixture's $C_2$ unsaturates, to form a product comprising $\geq 1.0$ wt. % of $C_{3+}$ aldehyde and/or $\geq 1.0$ wt. % $C_{3+}$ alcohol based on the weight of the product, wherein the $C_{3+}$ aldehyde is propanal and the $C_{3+}$ alcohol is propanol.

2. The process of claim 1, wherein the conversion of step (d) includes hydroformylation, the hydroformylation being conducted at least partially in the vapor phase under catalytic conversion conditions in the presence of a catalytically effective amount of a catalyst comprising at least one of cobalt, iron, iridium, or rhodium.

3. The process of claim 1, wherein:
   (i) the first mixture comprises 1.0 wt. % to 50.0 wt. % of the oxygenate based on the weight of the first mixture, and
   (ii) the second mixture has at least one of (1) an acetylene:ethylene molar ratio in the range of about 0.5 to about 20.0, (2) a CO:$C_2$ unsaturates molar ratio in the range of 0.15 to 2.0, (3) a carbon dioxide:$C_2$ unsaturates molar ratio $\leq 0.30$; or (4) a molecular hydrogen:acetylene molar ratio $\geq 0.75$.

4. The process of claim 1, further comprising:
   (e) providing a fourth mixture, and at least partially oxidizing the fourth mixture in a second region to produce a fifth mixture, the first and second regions being at least partially coextensive;
   wherein:
   (i) the fourth mixture comprises fuel and oxidant;
   (ii) the fifth mixture comprises water and/or carbon dioxide; and
   (iii) the exposing of the first mixture and the oxidizing of the fourth mixture occur at substantially different times.

5. The process of claim 4, further comprising repeating steps (a)-(e) in sequence, wherein (i) at least a portion of the fifth mixture is conducted away from the second region before step (a) and (ii) the exposure temperature in the first region results at least in part from the heat generated during the oxidizing of the fourth mixture in the second region.

6. The process of claim 4, further comprising at least one of:
   (i) separating from the fifth mixture a byproduct comprising oxygenate and utilizing at least a portion of the separated byproduct to produce the first and/or fourth mixtures; or
   (ii) separating from the second mixture a second byproduct comprising hydrocarbon and hydrogen and utilizing at least a portion of the separated second byproduct to produce the first and/or fourth mixtures.

7. The process of claim 3, wherein the transferred mixture comprises the third mixture, the third mixture being derived from the second mixture by:
   (i) separating from the second mixture at least one of acetylene, $C_{3+}$, heteroatom species, hydrogen, diluent, or saturated hydrocarbons; and/or
   (ii) combining carbon monoxide and/or molecular hydrogen, with the second mixture.

8. The process of claim 7, further comprising converting at least a portion of the separated acetylene to one or more of ethylene, ethylene glycol, acetic acid, acrylic acid, benzene, toluene, or xylene, styrene, or butadiene; the acetylene conversion being conducted in the presence of hydrogen and/or carbon monoxide separated from the product.

9. The process of claim 4, wherein the process further comprises at least one of (f) (i) contacting at least a portion of the product and molecular hydrogen in the vapor phase in the presence of a second catalyst, the second catalyst containing a catalytically effective amount of at least one element from Group VIII of the Periodic Table to produce a second product comprising $C_{3+}$ olefin and (ii) polymerizing at least a portion of the $C_{3+}$ olefin or (g) condensing the product to one or more oligomers of order $\geq 2$.

10. The process of claim 1, wherein the first mixture comprises $\geq 50.0$ ppm sulfur, the weight percents being based on the weight of the first mixture.

11. The process of claim 1, wherein:
   (i) the first mixture has a hydrogen content in the range of 20.0 wt. % to 25.0 wt. % based on the weight of the first mixture; and
   (ii) the first mixture comprises 5.0 wt. % to 25.0 wt. % of molecular hydrogen based on the weight of the first mixture, at least 15.0 wt. % of the molecular hydrogen in the first mixture being derived from the second mixture and/or the product.

12. The process of claim 1, wherein:
   (i) the exposing of step (b) is conducted under high-severity conditions; and
   (ii) the first mixture comprises 10.0 wt. % to 95.0 wt. % hydrocarbon and 5.0 wt. % to 60.0 wt. % oxygenate based on the weight of the first mixture.

13. The process of claim 8, further comprising:
   dividing the second mixture into first and second portions, the third mixture being derived from the first portion, and catalytically converting at least a portion of the second portion's acetylene to a third product comprising at least one of ethylene, ethylene glycol, acetic acid, acrylic acid, benzene, toluene, or xylene, styrene, or butadiene.

14. The process of claim 13, wherein the acetylene conversion catalyst comprises at least one of Ni, Pd, or Pt; and further comprising one or more of:
   (i) polymerizing at least a portion of the third product's ethylene;
   (ii) polymerizing at least a portion of the third product's styrene and/or butadiene; or (iii) copolymerizing at least a portion of the second product's propylene with at least a portion of one or more of the third product's ethylene, butadiene, or styrene.

15. The process of claim 8, further comprising:
(i) converting at least a portion of the first product to propylene;
(ii) polymerizing at least a portion of the propylene;
(iii) polymerizing at least a portion of the ethylene converted from the acetylene; or (iv) copolymerizing (i) at least a portion of the ethylene converted from the acetylene and (ii) at least a portion of the propylene.

* * * * *